(12) United States Patent
Aebersold et al.

(10) Patent No.: US 7,183,116 B2
(45) Date of Patent: Feb. 27, 2007

(54) METHODS FOR ISOLATION AND LABELING OF SAMPLE MOLECULES

(75) Inventors: Rudolf H. Aebersold, Mercer Island, WA (US); Huilin Zhou, San Diego, CA (US); Beate Rist, Giesen (DE); George J. Vella, Medway, MA (US); Subhasish Purkayastha, Acton, MA (US); Sasi Pillai, Littleton, MA (US)

(73) Assignees: The Institute For Systems Biology, Seattle, WA (US); University of Washington, Seattle, WA (US); Applera Corporation, Norwalk, CT (US)

(*) Notice: Subject to any disclaimer, the term of this patent is extended or adjusted under 35 U.S.C. 154(b) by 0 days.

(21) Appl. No.: 09/858,198

(22) Filed: May 14, 2001

(65) Prior Publication Data

US 2002/0168644 A1   Nov. 14, 2002

(51) Int. Cl.
*G01N 24/00* (2006.01)
*G01N 33/68* (2006.01)
*G01N 33/92* (2006.01)
*C12Q 1/68* (2006.01)

(52) U.S. Cl. .................. 436/86; 435/6; 436/71; 436/172; 436/173; 436/501; 530/402; 530/405

(58) Field of Classification Search ............ 436/173, 436/71, 86, 501, 172; 435/6; 530/412, 415, 530/402, 405
See application file for complete search history.

(56) References Cited

U.S. PATENT DOCUMENTS 6,057,096 A   5/2000   Rothschild et al.

FOREIGN PATENT DOCUMENTS

| WO | WO 99/02728 | 1/1999 |
| WO | WO 00/11208 | 3/2000 |
| WO | WO 01/96869 | 12/2001 |
| WO | WO 02/48717 | 6/2002 |

OTHER PUBLICATIONS

Bodanszky and Bodanszky *The Practice of Peptide Synthesis*, vol. 21 Springer-Verlag, New York (1984), Table of Contents only.
Brancia et al., "A combination of chemical derivatisation and improved bioinformatic tools optimises protein identification for proteomics," *Electrophoresis* 22:552-559 (2001).
Glazer et al., "Laboratory Techniques in Biochemistry and Molecular Biology: Chemical Modification of Proteins," *Elsevier Biomedical Press*, New York Chapter 3, pp. 68-120 (1975).
Gygi et al., "Evaluation of two-dimensional gel electrophoresis-based proteome analysis technology," *Proc. Natl. Acad. Sci. USA* 97:9390-9395 (2000).
Gygi et al., "Quantitative analysis of complex protein mixtures using isotope-coded affinity tags," *Nature Biotechnol.* 17:994-999 (1999).
Houghten, R. "General method for the rapid solid-phase synthesis of large numbers of peptides: specificity of antigen-antibody interaction at the level of individual amino acides," *Proc. Natl. Acad. Sci. USA*, 82:5131-5135 (1985).
Hoving et al., "A method for the chemical generation of N-terminal peptide sequence tags for rapid protein identification," *Anal. Chem.* 72:1006-1014 (2000).
Merrifield, R.B. "Solid Phase Peptide Synthesis," *J. Am. Chem. Soc.* 85:2149-2154 (1963).
Munchbach et al., "Quantitation and Facilitated de Novo Sequencing of Proteins by Isotopic N-Terminal Labeling of Peptides with a Fragmentation-Directing Moiety," *Anal. Chem.* 72:4047-4057 (2000).
Wilson and Czarnik, eds., *Combinatorial Chemistry: Synthesis and Application*, John Wiley & Sons, New York (1997). Table of Contents only.
Zhou et al., "A systematic approach to the analysis of protein phosphorylation," *Nature Biotechnol.* 19:375-378 (2001).
Aebersold et al., "Mass spectrometry in proteomics," *Chem. Reviews* 101(2):269-295 (2001).
Geysen et al., "Isotope or mass encoding of combinatorial libraries," *Chem. Biol.* 3:679-688 (1996).
Zhou et al., "Quantitative proteome analysis by solid-phase isotope tagging and mass spectrometry," *Nature Biotech.* 19:512-515 (2002).

*Primary Examiner*—Mary E. Ceperley
(74) *Attorney, Agent, or Firm*—McDermott Will & Emery LLP

(57) ABSTRACT

The invention provides methods for labeling a molecule by contacting a sample molecule with a solid support coupled to a chemical group comprising a cleavable functional group, one or more functional groups, and a reactive group for the sample molecule, under conditions allowing the sample molecule to covalently bind to the reactive group; and cleaving the cleavable functional group, thereby releasing the sample molecule comprising the one or more functional groups, which can be a tag. The invention also provides a solid support covalently coupled to a chemical group comprising a cleavable functional group, a mass spectrometry tag and a reactive group for covalently attaching a sample molecule, wherein the cleavable functional group, the tag and the reactive group are positioned relative to each other to allow transfer of the tag to the sample molecule upon cleavage of the cleavable functional group.

57 Claims, 13 Drawing Sheets

SEQUENCE LISTING

```
<160> NUMBER OF SEQ ID NOS: 2

<210> SEQ ID NO 1
<211> LENGTH: 9
<212> TYPE: PRT
<213> ORGANISM: Unknown
<220> FEATURE:
<223> OTHER INFORMATION: laminin B

<400> SEQUENCE: 1

Cys Asp Pro Gly Tyr Ile Arg Ser Arg
 1               5
```

```
<210> SEQ ID NO 2
<211> LENGTH: 8
<212> TYPE: PRT
<213> ORGANISM: Unknown
<220> FEATURE:
<223> OTHER INFORMATION: phosphoangiotensin

<400> SEQUENCE: 2

Asp Arg Val Tyr Ile His Pro Phe
 1               5
```

METHODS FOR ISOLATION AND LABELING OF SAMPLE MOLECULES

This invention was made with government support under grant number 1R33CA84698-0 awarded by the National Cancer Institute. The government has certain rights to the invention.

BACKGROUND OF THE INVENTION

This invention relates generally to proteome analysis and more specifically to methods for transferring functional groups to molecules in a sample for analysis and quantitation of the molecules.

The classical biochemical approach to study biological processes has been based on the purification to homogeneity by sequential fractionation and assay cycles of the specific activities that constitute a process, the detailed structural, functional and regulatory analysis of each isolated component, and the reconstitution of the process from the isolated components. The Human Genome Project and other genome sequencing programs are turning out in rapid succession the complete genome sequences of specific species and, thus, in principle the amino acid sequence of every protein potentially encoded by that species. It is to be expected that this information resource unprecedented in the history of biology will enhance traditional research methods and catalyze progress in fundamentally different research paradigms, one of which is proteomics.

Efforts to sequence the entire human genome along with the genomes of a number of other species have been extraordinarily successful. The genomes of 46 microbial species (TIGR Microbial Database; www.tigr.org) have been completed and the genomes of over one hundred twenty other microbial species are in the process of being sequenced. Additionally, the more complex genomes of eukaryotes, in particular those of the genetically well characterized unicellular organism *Saccharomyces cerevisiae* and the multicellular species *Caenorhabditis elegans* and *Drosophila melanogaster* have been sequenced completely. Furthermore, "draft sequence" of the rice, human and *Arabidopsis* genomes have been published. Even in the absence of complete genomic sequences, rich DNA sequence databases have been made publicly available, including those containing over 2.1 million human and over 1.2 million murine expressed sequence tags (ESTs).

ESTs are stretches of approximately 300 to 500 contiguous nucleotides representing partial gene sequences that are being generated by systematic single pass sequencing of the clones in cDNA libraries. On the timescale of most biological processes, with the notable exception of evolution, the genomic DNA sequence can be viewed as static, and a genomic sequence database therefore represents an information resource akin to a library. Intensive efforts are underway to assign "function" to individual sequences in sequence databases. This is attempted by the computational analysis of linear sequence motifs or higher order structural motifs that indicate a statistically significant similarity of a sequence to a family of sequences with known function, or by other means such as comparison of homologous protein functions across species. Other methods have also been used to determine function of individual sequences, including experimental methods such as gene knockouts and suppression of gene expression using antisense nucleotide technology, which can be time consuming and in some cases still insufficient to allow assignment of a biological function to a polypeptide encoded by the sequence.

The proteome has been defined as the protein complement expressed by a genome. This somewhat restrictive definition implies a static nature of the proteome. In reality the proteome is highly dynamic since the types of expressed proteins, their abundance, state of modification, subcellular locations, and interactions with other biomolecules such as polypeptides and nucleic acids are dependent on the physiological state of the cell or tissue. Therefore, the proteome can reflect a cellular state or the external conditions encountered by a cell, and proteome analysis can be viewed as a genome-wide assay to differentiate and study cellular states and to determine the molecular mechanisms that control them. Considering that the proteome of a differentiated cell is estimated to consist of thousands to tens of thousands of different types of proteins, with an estimated dynamic range of expression of at least 5 orders of magnitude, the prospects for proteome analysis appear daunting. However, the availability of DNA databases listing the sequence of every potentially expressed protein combined with rapid advances in technologies capable of identifying the proteins that are actually expressed now make proteomics a realistic proposition. Mass spectrometry is one of the essential legs on which current proteomics technology stands.

Quantitative proteomics is the systematic analysis of all proteins expressed by a cell or tissue with respect to their quantity and identity. The proteins expressed in a cell, tissue, biological fluid or protein complex at a given time precisely define the state of the cell or tissue at that time. The quantitative and qualitative differences between protein profiles of the same cell type in different states can be used to understand the transitions between respective states. Traditionally, proteome analysis was performed using a combination of high resolution gel electrophoresis, in particular two-dimensional gel electrophoresis, to separate proteins and mass spectrometry to identify proteins. This approach is sequential and tedious, but more importantly is fundamentally limited in that biologically important classes of proteins are essentially undetectable (Gygi et al., *Proc. Natl. Acad. Sci. USA* 97:9390–9395 (2000)).

The completion of the genomic sequence of a number of species has catalyzed a new approach to biology typically referred to as discovery science. The essence of discovery science is the systematic and quantitative analysis of all the members of a particular class of molecules expressed by a cell or tissue. Exemplary implementations of discovery science include the systematic analysis of mRNA molecules expressed by a cell or tissue by gene expression arrays and quantitative proteomics, the systematic analysis of the proteins contained in a biological sample. A main objective of discovery science is the description of the state of a cell or tissue (activity, pathology, stress) based on the data obtained from the systematic measurement of biomolecules and the identification of the molecular mechanisms that control the transition of a cell from one state to the other by the comparative analysis of the molecular composition of cells representing the two states. For the molecular description of a cellular state and mechanisms controlling it as many parameters as possible are desirable. Current expression array methods allow the systematic analysis of the mRNA molecules in a cell.

Recently, a method based on a class of reagents termed isotope coded affinity tags and mass spectrometry has been described that is suitable to systematically identify and quantify the proteins present in biological samples. Other properties relevant to the state of a cell, such as protein phosphorylation and other post translational modifications, and the quantitative profiles of biomolecules other than proteins or nucleic acids, for example, lipids, second messengers, metabolites, are difficult to measure systematically and quantitatively with current technology.

Thus, there exists a need for rapid, efficient, and cost effective methods for the analysis of molecules in a cell. The present invention satisfies this need and provides related advantages as well.

SUMMARY OF THE INVENTION

The invention provides methods for labeling a molecule by contacting a sample molecule with a solid support coupled to a chemical group comprising a cleavable functional group, one or more functional groups, and a reactive group for the sample molecule, under conditions allowing the sample molecule to covalently bind to the reactive group; and cleaving the cleavable functional group, thereby releasing the sample molecule comprising the one or more functional groups, which can be a tag. The invention also provides a solid support covalently coupled to a chemical group comprising a cleavable functional group, a mass spectrometry tag and a reactive group for covalently attaching a sample molecule, wherein the cleavable functional group, the tag and the reactive group are positioned relative to each other to allow transfer of the tag to the sample molecule upon cleavage of the cleavable functional group.

BRIEF DESCRIPTION OF THE DRAWINGS

FIG. 2 shows liquid chromatography-mass spectrometry (LC-MS) analysis of the peptide laminin B following reduction with tris(2-carboxyethyl)phosphine (TCEP) and the control peptide phosphoangiotensin.

FIG. 3 shows LC-MS of a mixture of reduced laminin B and phosphoangiotensin following contact with beads as shown in FIG. 1.

FIG. 4 shows LC-MS analysis of laminin B photo-cleaved from beads as treated in FIG. 3.

FIG. 6 shows LC-MS analysis of phosphoangiotensin modified with SATA.

FIG. 7 shows LC-MS analysis of SATA treated phosphoangiotensin further treated with hydroxylamine and reduction with TCEP, as shown in FIG. 5.

DETAILED DESCRIPTION OF THE INVENTION

Figure 1:
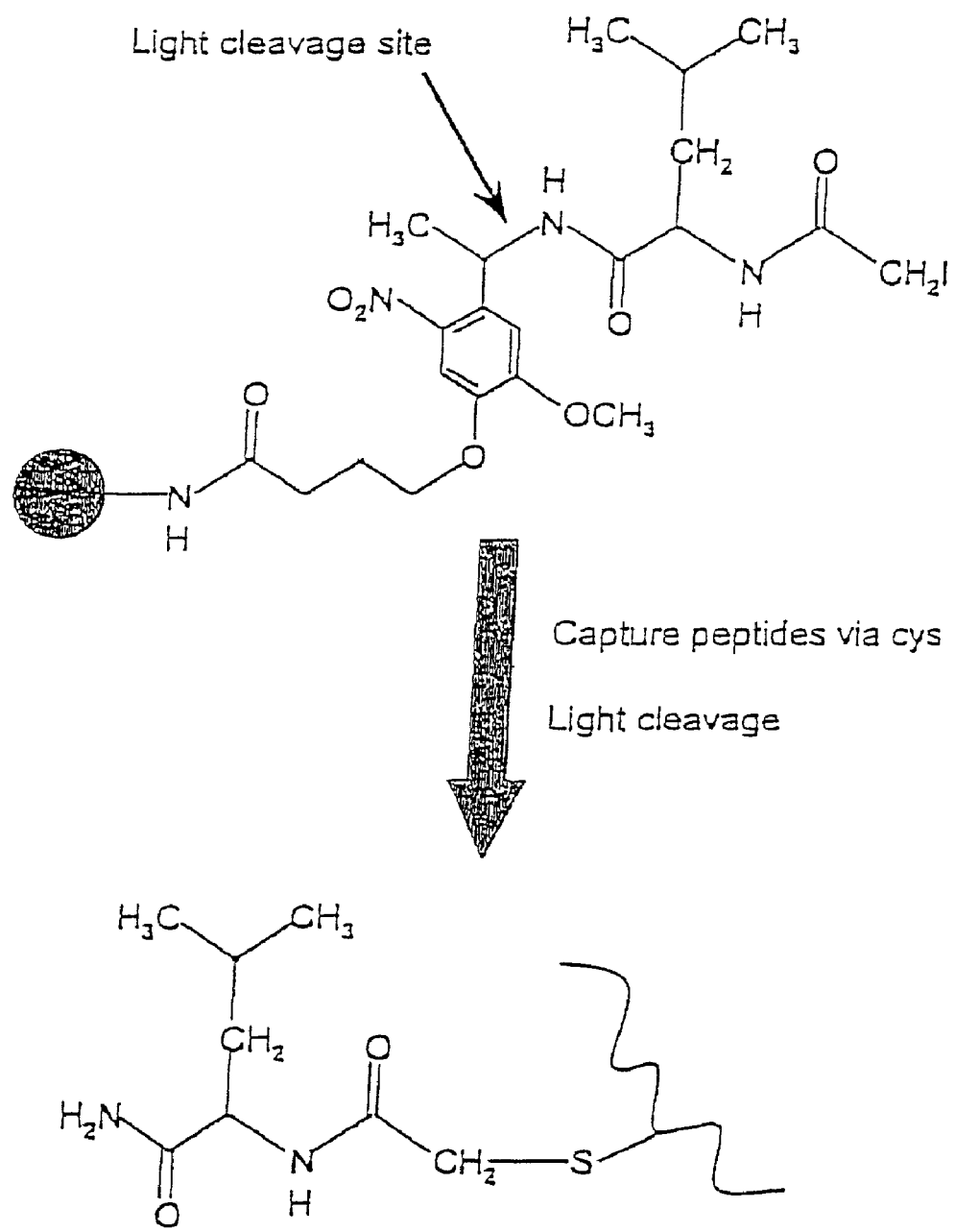
FIG. 1 shows a schematic diagram of a solid phase based approach to capture polypeptides via a photo-cleavable linker that allows light captured recovery of the polypeptides. The linker is constructed such that upon cleavage, specific functional groups are transferred to the released polypeptides.

The invention provides methods and compositions for labeling molecules in a sample by capturing the molecules on a solid support with a chemical group that allows transfer of desirable functional groups, including tags useful for enhanced detection and to facilitate identification and quantitation of tagged molecules, to the molecules. The methods are advantageous in that they can be used to selectively isolate and label molecules from a sample, allowing quantitative analysis of complex mixtures of analytes, including analysis by methods such as mass spectrometry. Thus, the methods can be used to isolate essentially all of a particular class of molecules or a subset of molecules, for example, essentially all polypeptides or the subset of phosphoproteins, glycoproteins, or otherwise modified polypeptides.

Using general covalent capture-and-release chemistries, specific functional groups can be transferred to the components of a complex sample. Furthermore, by incorporating the ability to release a captured molecule, the methods can also advantageously be used to isolate or purify sample molecules, which can be useful for reducing the complexity of a sample being analyzed. The methods are well suited for quantitative proteome analysis, for the systematic and quantitative analysis of protein phosphorylation and other post translational modifications and can be extended to the systematic and quantitative analysis of molecules other than proteins and peptides. Moreover, the methods of the invention are advantageous in that sample molecules can be efficiently captured and released, allowing the use of smaller amounts of starting sample, which is particularly useful for analyzing complex biological samples for proteomics analysis.

The methods of the invention are particularly useful for identification and quantitative analysis of the molecules contained in biological samples, in particular the analysis of proteins for quantitative proteomics. The methods can also be used for the systematic, quantitative analysis of protein phosphorylation or other modifications on otherwise modified proteins. The invention also provides reagents that are useful for labeling molecules. In addition to proteomics analysis, the methods are also useful for the systematic and quantitative analysis of other biomolecules in addition to proteins. The methods are particularly useful for transferring labels or tags to molecules suitable for mass spectrometry (MS) analysis.

As used herein, the term "polypeptide" refers to a peptide or polypeptide of two or more amino acids. A polypeptide can also be modified by naturally occurring modifications such as post-translational modifications or synthetic modifications, including phosphorylation, lipidation, prenylation, palmitylation, myristylation, sulfation, hydroxylation, acetylation, glycosylation, ubiquitination, addition of prosthetic groups or cofactors, formation of disulfide bonds, proteolysis, assembly into macromolecular complexes, and the like.

A polypeptide includes small polypeptides having a few or several amino acids as well as large polypeptides having several hundred or more amino acids. Usually, the covalent bond between the two or more amino acid residues is an amide bond. However, the amino acids can be joined together by various other means known to those skilled in the peptide and chemical arts. Therefore, the term polypeptide is intended to include molecules which contain, in whole or in part, non-amide linkages between amino acids, amino acid analogs, and mimetics. Similarly, the term also includes cyclic polypeptides and other conformationally constrained structures.

A modification of a polypeptide, particularly ligand polypeptides, can also include non-naturally occurring derivatives, analogues and functional mimetics thereof generated by chemical synthesis, provided that such polypeptide modification displays a similar functional activity compared to the parent polypeptide. For example, derivatives can include chemical modifications of the polypeptide such as alkylation, acylation, carbamylation, iodination, or any modification that derivatizes the polypeptide. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine. Also included as derivatives or analogues are those polypeptides which contain one or more naturally occurring amino acid derivatives of the twenty standard amino acids, for example, 4-hydroxyproline, 5-hydroxylysine, 3-methylhistidine, homoserine, ornithine or carboxyglutamate, and can include amino acids that are not linked by peptide bonds.

A particularly useful polypeptide derivative includes modification to incorporate desirable functional characteristics using the methods disclosed herein. Such modifications include the incorporation of a label or tag, particularly labels or tags useful for MS analysis.

As used herein, the term "nucleic acid" when used in reference to a component of a biochemical system, is intended to mean two or more nucleotides covalently bonded together such as deoxyribonucleic acid (DNA) or ribonucleic acids (RNA) and including, for example, single-stranded and a double-stranded nucleic acid. The term is similarly intended to include, for example, genomic DNA, cDNA, mRNA and synthetic oligonucleotides corresponding thereto which can represent the sense strand, the antisense strand or both.

As used herein, the term "amino acid" is intended to mean both naturally occurring and non-naturally occurring amino acids as well as amino acid analogs and mimetics. Naturally occurring amino acids include the 20 (L)-amino acids utilized during protein biosynthesis as well as others such as 4-hydroxyproline, hydroxylysine, desmosine, isodesmosine, homocysteine, citrulline and ornithine, for example. Non-naturally occurring amino acids include, for example, (D)-amino acids, norleucine, norvaline, p-fluorophenylalanine, ethionine and the like. Amino acid analogs include modified forms of naturally and non-naturally occurring amino acids. Such modifications can include, for example, substitution or replacement of chemical groups and moieties on the amino acid or by derivitization of the amino acid. Amino acid mimetics include, for example, organic structures which exhibit functionally similar properties such as charge and charge spacing characteristic of the reference amino acid. For example, an organic structure which mimics lysine (Lys or K) would have a positive charge moiety located in similar molecular space and having the same degree of mobility as the $\epsilon$-amino group of the side chain of the naturally occurring Lys amino acid. Mimetics also include constrained structures so as to maintain optimal spacing and charge interactions of the amino acid or of the amino acid functional groups.

As used herein, a "functional group" is any chemical group that has desirable functional properties. A desirable functional property is any property that imparts a desirable chemical characteristic to a molecule. A functional group can include a group that changes the physicochemical properties of a molecule, for example, changing the mass, charge, hydrophobicity, and the like. A particularly useful functional group is a label or tag, for example, fluorophores, chromophores, spin labels, isotope distribution tags, and the like.

As used herein, the term "label" is intended to mean any moiety that can be attached to a molecule that results in a change in mass of that molecule. The label can be bound to the molecule either covalently or non-covalently, although generally the label will be covalently bound. It is understood that, where a non-covalent interaction occurs between the label and the molecule, the non-covalent interactions are of sufficiently high affinity to allow the label to remain bound to the molecule during chemical and/or physical manipulations used in methods of the invention.

A particularly useful label is a mass label useful for analysis of a sample by MS. The change in mass of the molecule due to the incorporation of a mass label should be within the sensitivity range of the instrument selected for mass determination. In addition, one skilled in the art will know or can determine the appropriate mass of a label for molecules of different sizes and different compositions. Moreover, when using heavy and light mass labels, for example, for differential labeling of molecules, a mass difference as small as between about 1–3 mass units can be used or as large as greater than about 10 mass units. Mass labels suitable for differentially labeling two samples are chemically identical but differ in mass.

As used herein, a "tag" refers to a label that is detectable. The tag imparts a characteristic to a molecule such that it can be detected by any of a variety of analytical methods, including MS, chromatography, fluorography, spectrophotometry, immunological techniques, and the like. A tag can be, for example, an isotope, fluor, chromagen, ferromagnetic substance, luminescent tag, or an epitope tag recognized by an antibody or antibody fragment. A particularly useful tag is a mass tag, which is a mass label suitable for detection and analysis of a molecule by MS. Exemplary mass tags include, for example, a stable isotope tag, an isotope distribution tag, a charged amino acid, differentially isotopically labeled tags, and the like. A tag can also be a gas-phase basic group such as pyridyl or a hydrophobic group. A tag can also be an element having a characteristic isotope distribution, for example, chlorine, bromine, or any elements having distinguishable isotopic distribution. Additionally, a tag can have a bond that breaks in a collision cell or ion source of a mass spectrometer under appropriate conditions and produces a reporter ion.

A tag can also be an affinity tag that allows isolation of a molecule coupled to the affinity reagent by binding to a cognate binding partner of the affinity tag. For polypeptide tagging, a polypeptide or polypeptides in a sample can be denatured, optionally reduced, and a chemically reactive group of the polypeptide covalently derivatized with a chemical modification reagent. Tagged polypeptides can be easily isolated from untagged polypeptides and other components within a sample, which reduces the complexity of the sample that is to be analyzed by mass spectrometry. Such affinity tagging can similarly be applied to other molecules such as nucleic acids, lipids, carbohydrate, second messengers, metabolites, and the like. Furthermore, a tag can be introduced by a chemical or enzymatically catalyzed reaction.

As used herein, a "cleavable functional group" is a chemical group that can be cleaved by a variety of methods, including input of energy, a chemical, an enzyme, and the like. For use in methods of the invention, the cleavable functional group is generally specific, that is, one which can be specifically cleaved without altering or damaging the molecule being cleaved or which relatively uniformly alters the molecule in a reproducible manner. For example, the cleavable functional group can be a photo-cleavable group. In such a case, the photo-cleavable group is generally cleaved at a wavelength of light that does not damage the molecule being released, for example, in the ultraviolet to visible range (see Example I).

The cleavable functional group can also be a chemical cleavable group cleavable by a chemical such as an acid or base. If desired, a chemical cleavage reaction can be carried out under relatively mild conditions in which the chemical cleavable group is essentially the only chemical bond cleaved. A chemical cleavable group can also be a group cleavable by a chemical such as CNBr, which can cleave a methionine residue. CNBr can be particularly useful for releasing a molecule if a chemical cleavable group such as methionine has been added to the molecule, particularly in a polypeptide that does not have a methionine residue. Suitable chemical cleavable groups are well known to those skilled in the art (see, for example Wilson and Czarnik, eds., *Combinatorial Chemistry: Synthesis and Application*, John Wiley & Sons, New York (1997); Merrifield, *J. Am. Chem. Soc.* 85:2149 (1964); Bodanszky, M., *Principles of Peptide Synthesis* (Springer-Verlag, 1984); Houghten, *Proc. Natl. Acad. Sci., USA* 82:5131 (1985).

The cleavable functional group can also be an enzymatic cleavable group. For example, a protease can be used to cleave a cleavable functional group having a suitable recognition sequence for the protease. Particularly useful proteases are endopeptidases such as factor Xa, tobacco etch virus (TEV) protease, trypsin, chymotrypsin, *Staphylococcus aureus* protease, submaxillaris protease, and the like. The protease can be selected based on the incorporation of a particular cleavable recognition sequence as a functional group. Other considerations for selecting a protease include the presence or absence of a recognition sequence in the molecule being captured and released.

For example, a rare cleaving protease such as TEV protease or factor Xa can be used to cleave a functional group containing the corresponding protease recognition sequence, resulting in release of the captured molecule. Such rare cleaving proteases are particularly useful for releasing an intact polypeptide molecule since the recognition sequence for these proteases would not occur in the vast majority of polypeptides. Alternatively, a polypeptide sample can be treated with a specific protease, and the digested peptides isolated by the methods disclosed herein. In such a case, the captured peptides would not contain a recognition sequence for the protease used for cleavage since the polypeptide has already been digested. In addition, if desired, an intact polypeptide can be captured and digested with a protease after binding to the solid support, resulting in the incorporation and release of a label on the peptide fragment of the polypeptide that was captured on the solid support. Thus, protease digestion can be used before or after capture of a sample molecule, in particular polypeptide sample molecules, as desired.

In addition to proteases, a cleavable functional group can be a recognition sequence for an endonuclease such as a restriction enzyme. Thus, an appropriate recognition sequence for a restriction enzyme can be incorporated as a cleavable functional group and cleaved with the respective restriction enzyme. It is understood that such a nucleotide functional group can be useful for capturing and releasing a nucleic acid or a polypeptide, or any other type of molecule, as desired. Similarly, a protease recognition sequence can be useful for capturing and releasing a polypeptide, nucleic acid or any other type of molecule, as desired.

As used herein, the term "reactive group" is intended to mean any of a variety of chemical groups having useful chemical properties suitable for reacting and covalently binding to a molecule such as a polypeptide, nucleic acid, lipid, carbohydrate, a second messenger, a metabolite, and the like. For example, a reactive group can react with carboxyl groups found in Asp or Glu, or the reactive group can react with other amino acids such as His, Tyr, Arg, and Met. A reactive group can also react with amines such as Lys, for example, imidoesters and N-hydroxysuccinimidyl esters. In addition, a reactive group can also react with oxygen or sulfur using chemistry well known in the art. A reactive group can also react with a phosphate group for selective labeling of phosphopeptides or nucleic acids, or with other covalently modified peptides, including glycopeptides, lipopeptides, or any of the covalent polypeptide modifications disclosed herein.

As used herein, the term "isotopic label" or "isotope tag" refers to a chemical group which can be generated in two distinct isotopic forms, for example, heavy and light isotopic versions of the constituent elements making up the chemical group. Such constituent elements include, for example, carbon, oxygen, hydrogen, nitrogen, and sulfur. In addition, other elements that are chemically or functionally similar can be substituted for the above naturally occurring elements. For example, selenium can be used as a substitute for sulfur. Particularly useful isotopic labels or tags are those that allow convenient analysis by MS. For example, heavy and light isotopic versions of an amino acid can be used to differentially isotopically label a polypeptide (see Example I).

As used herein, "coupled," or grammatical forms thereof, refers to the binding interaction between molecules. For example, a solid support can be coupled to a chemical group via binding interactions between a chemical moiety of the solid support and a chemical moiety of the chemical group. The binding interaction between coupled molecules can be covalent or non-covalent. Generally, a chemical group is coupled to a solid support or other molecule via covalent interactions. It is understood that, where a non-covalent interaction occurs between the solid support and coupled molecules, the non-covalent interactions are of sufficiently high affinity to remain bound during chemical and/or physical manipulations used in methods of the invention, for example, chemical modification or washing steps carried out on molecules bound to the solid support.

The invention provides a method for labeling a molecule by contacting a sample molecule with a solid support coupled to a chemical group comprising a cleavable functional group, one or more functional groups, and a reactive group for the sample molecule, under conditions allowing the sample molecule to covalently bind to the reactive group. The method can further include the step of cleaving the cleavable functional group, thereby releasing the sample molecule having one or more functional groups attached. The methods are advantageous in that a molecule in a complex sample mixture can be captured and labeled for convenient analysis and, due to the ability to be released from the solid support, can also be purified.

The invention provides methods that utilize a solid phase based approach to capture polypeptides or other molecules of interest covalently via a cleavable linker such as a photo-cleavable linker that allows light catalyzed recovery of the captured molecules. The cleavable linker is constructed such that, upon cleavage, specific functional groups are transferred to the released molecules. Such functional groups include, for example, stable isotope tags that enable accurate peptide quantification by mass spectrometry based on isotope dilution theory, isotope distribution tags that identify the tagged peptides or fragments thereof by their isotope distribution, charged amino acids, or other compounds that mediate efficient ionization in a mass spectrometer and direct the fragmentation pattern in the collision cell of a tandem mass spectrometer. Furthermore, the method allows the chemical or enzymatic modification, de-modification, cleavage or other manipulation of the molecules such as polypeptides while they are immobilized on the solid support. Although a photo-cleavable linker is particularly useful, it is understood that any linker that can be specifically cleaved can be used, as disclosed herein. Alternatives to photo-cleavable linkers include acid and base cleavable linkers, linkers cleavable by heat and linkers containing a target cleavage site for enzymes, as described herein.

The methods of the invention are based on the advantageous use of solid phase chemistry to immobilize molecules from a sample and allow the convenient transfer of a label such as a tag to the captured sample molecules. The method is based on the attachment of a chemical group to a solid support. The chemical group has features, which are exemplified in FIG. 1. One feature of the chemical group is a cleavable functional group that allows reversible capture and release of a molecule. A second feature of the chemical group is one or more functional groups having desirable chemical properties. Such a functional group can be, for example, a label or tag convenient for subsequent analysis of the molecule or a chemical moiety that imparts a desirable chemical property on the molecule such as a change in charge, hydrophobicity, or mass. A third feature of the chemical group is a reactive group that allows covalent binding of the chemical group to a molecule in a sample. These three features are arranged on the chemical group such that a sample molecule can be captured via the reactive group and, upon cleavage, the functional groups are transferred to the released molecule (see FIG. 1).

The chemical group also contains a chemical moiety that allows the chemical group to be attached to a solid support while at the same time allowing the above-described features to be exploited. The chemical group having the above-described features can be synthesized on a solid support by sequential addition of chemical moieties imparting the features or can be synthesized as a chemical group and then attached to the solid support, if desired.

A particular embodiment of a method of the invention is illustrated in FIG. 1. A chemical group having a cleavable functional group, one or more desired functional groups such as a tag, and a reactive group is coupled to the solid support. FIG. 1 shows a photo-cleavable linker with an amino functionality that is covalently attached to the solid support. This photo-cleavable linker allows light-initiated cleavage of molecules after they are captured on the solid phase. A linker molecule having desired specific functional groups is attached to the photo-cleavable linker via the amino functionality. Upon photo-cleavage, the linker molecule containing the functional groups is transferred to the captured molecule, represented as a peptide in FIG. 1, resulting in the transfer of desirable functional groups to the molecule. For example, as disclosed herein, the functional group transferred can be a stable isotope coded amino acid useful for quantitative mass spectrometry. Extending from the functional linker having one or more functional groups is a reactive group with specificity for a chemical moiety on the molecule, for example, a group reactive with amino, sulfhydryl, carboxy, or other groups of a polypeptide.

A molecule, for example, a molecule in a sample, is contacted with the solid support having a chemical group attached as described above. The molecules are incubated under conditions that allow covalent binding of the molecule to the solid support via the chemical group. One skilled in the art can readily determine appropriate conditions for allowing covalent coupling based on the reactive group on the chemical group and on the sample molecule.

In the particular embodiment exemplified in Example 1 and shown in FIG. 1, the solid phase support is a controlled pore glass bead to which the photo-cleavable linker has been attached via a silane linkage. The photo-cleavable linker shown in FIG. 1 can be cleaved with 360 nm UV light. A deuterated or non-deuterated amino acid such as leucine can used as the functional groups to be transferred to the polypeptide exemplified in Figure. If two different samples sources are used for a comparative or quantitative analysis, the two isotope tags will generally differ in mass by 7 or 10 mass units depending on the state of deuteration of leucine. As disclosed herein, other amino acids of different isotope distributions or molecules different from an amino acid can also be used as stable isotope tags. The peptide-reactive group shown in FIG. 1 is an iodoacetyl group that specifically reacts with sulfhydryl groups. Upon photo cleavage, the polypeptides illustrated in FIG. 1 are released with the addition of mass tags due to the modified leucine. Although exemplified with deuterated amino acids, it is understood that any suitable isotopic form, for example, isotopes of other constituent elements such as $^{13}C$, $^{15}N$, and the like, can be used in methods of the invention. Although non-radioactive isotopes are generally used even radioactive isotopes such as tritium can be used.

The invention additionally provides a composition comprising a solid support coupled to a chemical group comprising a cleavable functional group, a tag and a reactive group covalently linked to a sample molecule, wherein the cleavable functional group, the tag and the reactive group are positioned relative to each other to allow transfer of the tag to the sample molecule upon cleavage of the cleavable functional group. The invention further provides a composition comprising a solid support covalently coupled to a chemical group comprising a cleavable functional group, a mass spectrometry tag and a reactive group for covalently attaching a sample molecule, wherein the cleavable functional group, the tag and the reactive group are positioned relative to each other to allow transfer of the tag to the sample molecule upon cleavage of the cleavable functional group.

The methods of the invention are advantageous in that they provide the ability to selectively isolate a molecule and transfer of one or more functional groups, including a label or tag, onto the molecule upon release. Accordingly, the functionalities of the chemical group, that is, the cleavable functional group, one or more functional groups and the reactive group, are positioned relative to each other to allow transfer of a functional group to the molecule. Therefore, the functionalities of the chemical group will generally be arranged so that the functional group, for example, a tag, is positioned between the cleavable functional group and the reactive group, as illustrated in FIG. 1, allowing transfer of the functional group to the captured molecule upon cleavage of the cleavable functional group and release of the molecule.

The methods of the invention are advantageous since they utilize the ability to capture sample molecules, transfer a functional group to the molecules, and release the molecules with an attached functional group. Thus, the methods can be used to label a sample molecule and concomitantly purify the sample molecule in a single step. The incorporation of a cleavable functional group facilitates the release of the sample molecule with the attached functional group, which can then be further analyzed. Although the methods of the invention generally use a cleavable functional group, it is understood that the methods of the invention can also be used to transfer a functional group such as a label or tag without the need to release the captured molecule prior to further analysis. Use of methods of the invention in the absence of a cleavable chemical group cleavable by a chemical or enzymatic reaction is applicable to analytical methods such as MS, in particular, MALDI-TOF, in which a laser is used to cleave an attached molecule and ionize the molecule at the same time.

The methods of the invention can readily be applied to a wide variety of molecules. As described above, in some cases, a molecule can have a reactive chemical moiety suitable for the capture methods disclosed herein. However, if desired, the molecules can be modified to incorporate a desirable functional group, in particular a reactive group suitable for the capture methods disclosed herein.

For example, polypeptides that do not contain cysteine residues, that is, do not contain the natural amino acids containing a sulfhydryl side chain, would not bind to the solid-phase reagents shown in FIG. 1. While it is desirable in some cases to selectively isolate cysteine-containing polypeptides, in other cases it is desirable to isolate, identify and quantify other or additional polypeptides contained in a sample. For example, it is possible to synthesize amino-reactive groups such as succinimide esters as the reactive group of the solid-phase reagent. Alternatively, the molecules to be captured can be chemically modified to incorporate a specific functional group.

For example, in a specific embodiment disclosed herein, the primary amine groups of a polypeptide is modified to a sulfhydryl group, allowing the same SH-reactive solid phase beads as shown in FIG. 1 to be used to capture the polypeptide. In this strategy, an amino group of a polypeptide can be converted into a sulfhydryl group by the one-pot chemistry shown in FIG. 5. First, amino groups are modified by N-succinimidyl S-acetylthioacctate (SATA). Upon hydroxylamine treatment, followed by reduction with tris(2-carboxyethyl)phosphine (TCEP), the amino group of the peptide is converted into a sulfhydryl group. As exemplified herein, essentially every amino group in a sample molecule can be converted to a sulfhydryl group (see Example II). Modified peptides can be optionally purified, for example, by desalting on a C18 reverse phase cartridge, recovered and can then be attached to the beads such as those shown in FIG. 1.

Upon conversion of amino groups into sulfhydryl groups, the protonation site disappears. Therefore, charged amino acids such as lysine, instead of, for example, leucine, can be used to tag the polypeptides. In this way, the free amino group of the lysine side chain can provide the alternative site of protonation and the charge state of the peptide remains unchanged by this procedure. Other suitable groups for adding a tag containing a charged group include, for example, arginine, pyridyl, trimethylamine, and the like, which are strong bases in solution or gas phase, that is, groups that promote ionization. This is important since the charge state of peptides under typical mass spectrometry experiment affects the collision induced fragmentation in the mass spectrometer for peptide sequencing and detection.

Methods and chemistries for modifying amino acid side chains in polypeptides are well known to those skilled in the art (see, for example, Glazer et al., *Laboratory Techniques in Biochemistry and Molecular Biology: Chemical Modification of Proteins*, Chapter 3, pp. 68–120, Elsevier Biomedical Press, New York (1975), which is incorporated herein by reference; and Pierce Catalog (1994), Pierce, Rockford Ill.). Any of a variety of reactive groups can be incorporated into a chemical group for reacting with a sample molecule so long as the reactive group can be covalently coupled to a molecule such as a polypeptide. For example, a reactive group can react with carboxyl groups found in Asp or Glu, or the reactive group can react with other amino acids such as His, Tyr, Arg, and Met. A reactive group can also react with amines such as Lys, for example, imidoesters and N-hydroxysuccinimidyl esters. In addition, a reactive group can also react with oxygen or sulfur using chemistry well known in the art. A reactive group can also react with a phosphate group for selective labeling of phosphopeptides, or with other covalently modified peptides, including glycopeptides, lipopeptides, or any of the covalent polypeptide modifications disclosed herein. Additionally, one skilled in the art will know or can readily determine conditions for modifying polypeptides using known reagents, incubation conditions and time of incubation to obtain conditions optimal for modification of polypeptides or other molecules for use in methods of the invention.

Methods for modifying the amino-terminus of a polypeptide can also be used. In addition to the method exemplified herein for modifying an amino group, including the N-terminus (see Example II), other methods for modifying the N-terminus are well known to those skilled in the art (see, for example, Brancia et al., *Electrophoresis* 22:552–559 (2001); Hoving et al., *Anal. Chem.* 72:1006–1014 (2000); Munchbach et al., *Anal. Chem.* 72:4047–4057 (2000), each of which is incorporated herein by reference).

In addition, a reactive group can be generated on a molecule, which can subsequently be modified to incorporate a desired chemical moiety. For example, cleavage by CNBr results in a homoserine lactone. Accordingly, a polypeptide containing methionine can be chemically cleaved by CNBr to generate a homoserine lactone. The resulting homoserine lactone can be modified by an amine, allowing incorporation of a chemical group having a reactive amine.

The molecules can be modified chemically or enzymatically, as desired. For example, the molecules can be chemically modified using methods such as those described above. In addition, the molecules can be modified enzymatically. A captured molecule can be enzymatically modified to incorporate or remove a group from the molecule. For example, a polypeptide can be phosphorylated by a kinase or dephosphorylated by a phosphatase, or by any other enzyme having the ability to posttranslationally modify a polypeptide resulting in the addition or removal of a chemical moiety from the molecule. Similarly, a nucleic acid can be modified after capture by any of the well known enzymes that add or remove chemical moieties to or from a nucleic acid (see, for example, Sambrook et al., *Molecular Cloning: A Laboratory Manual,* 2nd ed., Cold Spring Harbor Press, Plainview, N.Y. (1989); Ausubel et al., *Current Protocols in Molecular Biology* (Supplement 47), John Wiley & Sons, New York (1999); Sambrook and Russel, *Molecular Cloning: A Laboratory Manual,* 3rd ed., Cold Spring Harbor Press, Cold Spring Harbor (2001)). Exemplary enzymes useful for modifying a captured molecule, including polypeptides or nucleic acids, include kinases, phosphatases, methylases, decarboxylases, and the like, or any enzyme capable of adding or removing a chemical moiety to or from a captured molecule.

The methods of the invention are advantageous in that, by capturing sample molecules, various chemical and/or enzymatic modifications can be performed on the attached molecules while the sample molecules remain bound to the solid support. Because the sample molecules remain bound to the solid support during physical, chemical and/or enzymatic manipulations, the yield of modified sample molecules is higher than solution phase methods. Thus, the methods of the invention can be used to capture at least about 5%, about 10%, about 20%, about 30%, abut 40%, about 50%, about 60%, about 70%, about 80%, about 90%, about 95%, about 98% or even essentially all of a particular class or classes of molecules. Furthermoe, the methods of the invention can be used to capture and release at least about 5%, about 10%, about 20%, about 30%, about 40%, about 50%, about 60%, about 70%, about 80%, about 90%, about 95%, about 98% or even essentially all of a particular class or classes of molecules in a sample that are contacted with the solid support. For example, as disclosed herein, essentially 100% of the molecule can be captured (see Example I). One skilled in the art can readily determine conditions optimized for capturing sample molecules and/or releasing sample molecules from the solid support.

The invention further provides a method for labeling a molecule. The method includes the steps of contacting a sample molecule with a solid support coupled to a chemical group comprising a cleavable functional group, one or more functional groups, and a reactive group for the sample molecule, under conditions allowing the sample molecule to covalently bind to the reactive group; modifying the sample molecule bound to the solid support; and cleaving the cleavable functional group, thereby releasing the modified sample molecule comprising one or more functional groups.

The methods of the invention can be used to modify captured molecules, as desired. For example, the methods can be used to capture polypeptides from a sample including both phosphorylated and non-phosphorylated polypeptides. A method systematically analyzing protein phosphorylation has recently been described (Zhou et al., *Nature Biotechnol.* 19:375–378 (2001)). Rather than carrying out chemical reactions in solution as in Zhou et al., the polypeptides can first be captured using the methods disclosed herein and modified while attached to the solid support (see Example IV). Alternatively, the methods disclosed herein for capturing and labeling a molecule can be applied after performing the reactions described in Zhou et al., supra, 2001, or any other chemical or enzymatic modifications.

The compositions and methods of the invention can be advantageously used in a variety of applications. One particularly useful application is quantitative protein expression analysis. For example, the methods and reagents disclosed herein can be used to impart specific isotopic signatures to a molecule such as a polypeptide contained in a complex sample. In one particular application of quantitative analysis, two or more samples can be compared (see FIG. 8, Example III). Quantitative analysis of peptides from two different samples can be achieved based on the concept of stable isotope dilution in a similar fashion as the ICAT technology for relative quantification of protein expression (Gygi et al., *Nature Biotechnol.* 17:994–999 (1999)). A differentially isotopically labeled molecule can be used to label two samples for comparison, for example, an amino acid such as a deuterated leucine or non-deuterated leucine, or other amino acids, which can be incorporated as mass tags for two different samples. The methods of the invention are advantageous in that both isolation of a molecule and incorporation of a tag such as a stable isotope are both achieved. Thus, the methods of the invention are particularly useful for quantitative mass spectrometric analysis.

As disclosed herein, incorporation of functional groups to a polypeptide can also be achieved through the amino groups of a peptide, which is particularly useful if the polypeptide to be analyzed does not contain free cysteine residues when applying a capture method based on the presence of sulfhydryl groups in a polypeptide. Since most polypeptides contain at least one amino group at its N-terminus, even polypeptides with no cysteine residues can be labeled with the solid phase based method to incorporate sulfhydryl groups into the polypeptide. In the case of a polypeptide in a sample having a blocked amino-terminus, such polypeptides can be fragmented to generate a free amino terminus on the cleaved fragments. Thus, the methods of the invention can be applied to the isolation of a variety of molecules using specific chemical modifications.

Furthermore, there is great structural flexibility in the choice of the transferred tags. The structure of the tag can therefore be deliberately chosen to achieve specific objectives. For example, very polar peptides can be made more hydrophobic and therefore better retained on reverse-phase columns by the transfer of a hydrophobic tag, a strong gas-phase basic group such as pyridyl can be transferred to direct fragmentation in the collision cell of a mass spectrometer, or elements with characteristic isotope distribution such as chlorine or bromine can be added to provide distinct isotopic signatures for the tagged peptides.

The methods of the invention can also be applied to the analysis of modified molecules, for example, polypeptides modified by post-translational modifications. For example, the methods can be applied to quantitative analysis of protein phosphorylation. Methods for the systematic analysis of protein phosphorylation has been previously described (Zhou et al., *Nature Biotechnol.* 19:375–378 (2001). A sequence of chemical reactions is carried out in solution for the selective isolation of phosphorylated peptides from complex peptide solutions containing phosphorylated and non-phosphorylated polypeptides in solution (Zhou et al., supra, 2001). The methods disclosed herein using solid phase capture and release can also be used for the selective isolation of phosphopeptides. Phosphorylated and non-phosphorylated polypeptides are captured on the solid phase beads, as disclosed herein. Once immobilized, a sequence of chemical reactions is carried out that lead to phosphate-specific labeling of phosphopeptides (Zhou et al., supra, 2001). The peptides are released by cleavage, imparting a stable isotope signature to each peptide for accurate quantification. The originally phosphorylated polypeptides, now converted to sulfhydryl groups, can be captured using the methods disclosed herein for isolating a sulfhydryl-containing molecule. The captured polypeptides can be washed free of non-phosphorylated peptides and released, for example, for mass spectrometric analysis. The methods of the invention disclosed herein have obvious advantages over the solution chemistry as the number of sample handling steps required to remove excess reagents after each chemical reaction are dramatically reduced and simplified.

In addition to phosphorylation, the methods of the invention can be readily applied to polypeptides having many different forms of post-translational modifications such as glycosylation, ubiquitination, acetylation, palmitylation, myristylation, and the like, as disclosed herein. The methods of the invention can thus be used to selectively isolate other post-translationally modified molecules, including polypeptides, with concomitant transfer of various functional groups to the peptides. Selective isolation of a particular type of post-translational modification can be achieved using methods of the invention. For example, an antibody having specific binding activity for ubiquitination can be used to isolate ubiquitinated polypeptides, allowing quantitative analysis of ubiquitination of polypeptides in much the same fashion of quantitative analysis of protein phosphorylation is achieved. Such methods can also be applied to other modifications of molecules, if desired.

Antibodies can also be used for subsequent analysis and/or isolation of sample molecules modified with an epitope tag. Methods for preparing antibodies are well known to those skilled in the art. The term antibody is used in its broadest sense to include polyclonal and monoclonal antibodies, as well as antigen binding fragments of such antibodies. An antibody useful in the invention, or antigen binding fragment of such an antibody, is characterized by having specific binding activity for a polypeptide or a peptide portion thereof of at least about $1 \times 10^5$ $M^{-1}$. Thus, Fab, F(ab')$_2$, Fd, Fv, single chain Fv (scFv) fragments of an antibody and the like, which retain specific binding activity for a polypeptide. Specific binding activity of an antibody for a polypeptide can be readily determined by one skilled in the art, for example, by comparing the binding activity of an antibody to a particular antigen versus a control antigen. Methods of preparing polyclonal or monoclonal antibodies and determining binding activity and/or specificity are well known to those skilled in the art (see, for example, Harlow and Lane, *Antibodies: A Laboratory Manual,* Cold Spring Harbor Laboratory Press (1988)).

Although the methods of the invention have generally been exemplified herein with polypeptides, it is understood that any of a variety of molecules in a sample can be readily labeled by the methods disclosed herein. In general, many classes of biomolecules such as oligonucleotides, metabolite, and the like, can be functionalized by the methods disclosed herein to incorporate desirable functional groups for improved qualitative or quantitative analysis. Therefore, the methods disclosed herein, allowing reversible capture and transfer of specific functional groups to a molecule is generally useful in many applications in the field of proteomics, other types of discovery science and quantitative biological analyses in general.

The methods of the invention can be used to efficiently capture and release a class of molecules such as polypeptides, nucleic acids, lipids, second messengers, metabolites, and the like, or a subset of such a class of molecules. If desired, the methods of the invention can also be used to capture two or more classes of molecules and/or a subset of those classes of molecule. For example, the methods can be used to capture both polypeptides and nucleic acids, or any combination of two or more classes of molecules, as desired.

The invention also provides a method for analyzing a molecule. The method includes the steps of contacting a sample molecule with a solid support coupled to a chemical group comprising a cleavable functional group, one or more functional groups, and a reactive group for the sample molecule, under conditions allowing the sample molecule to covalently bind to the reactive group; cleaving the sample molecule from the solid support, wherein one or more specific functional groups are transferred to the released sample molecule; and analyzing the released sample molecule. Any of a variety of analytical methods can be used including, for example, mass spectrometry, sequencing, liquid chromatography, spectrophotometry, fluoremtry, and the like. The methods of the invention are advantageous since the molecules can be covalently captured, allowing extensive washing to remove non-analyte materials prior to analysis. Furthermore, the functional groups to be transferred to the captured molecules can incorporate a functionality useful for facilitating further analysis of the molecules, for example, by adding a chromophore, fluorphore, mass tag, and the like.

Mass spectrometry is a particularly useful method for analyzing sample molecules. A variety of mass spectrometry systems can be employed to analyze sample molecules captured using the methods of the invention. Mass analyzers with high mass accuracy, high sensitivity and high resolution can be used and include, but are not limited to, matrix-assisted laser desorption time-of-flight (MALDI-TOF) mass spectrometers, ESI-TOF mass spectrometers and Fourier transform ion cyclotron mass analyzers (FT-ICR-MS). Other modes of MS include an electrospray process with MS and ion trap. In ion trap MS, fragments are ionized by electrospray or MALDI and then put into an ion trap. Trapped ions can then be separately analyzed by MS upon selective release from the ion trap. Fragments can also be generated in the ion trap and analyzed. The sample molecules labeled with a mass tag using methods of the invention can be analyzed, for example, by single stage mass spectrometry with a MALDI-TOF or ESI-TOF system. Furthermore, LC-MS/MS or LC-ESI-TOF can be used. It is understood that any MS methods and any combination of MS methods can be used to analyze a sample molecule.

The methods of the invention can be used to analyze molecules in a sample. The sample can be derived, for example, from a biological specimen. A specimen refers specifically to a sample obtained from an organism or individual. A specimen can be obtained from an individual as a fluid or tissue specimen. For example, a tissue specimen can be obtained as a biopsy such as a skin biopsy, tissue biopsy or tumor biopsy. A fluid specimen can be blood, serum, urine, saliva, cerebrospinal fluid or other bodily fluids. A fluid specimen is particularly useful in methods of the invention since fluid specimens are readily obtained from an individual. Methods for collection of specimens are well known to those skilled in the art (see, for example, Young and Bermes, in *Tietz Textbook of Clinical Chemistry,* 3rd ed., Burtis and Ashwood, eds., W. B. Saunders, Philadelphia, Chapter 2, pp. 42–72 (1999)). A specimen can also be a microbiological specimen, which can be derived from a culture of the microorganisms, including those cultured from a specimen from an individual. Thus, the methods of the invention can be used to analyze complex mixtures in biological samples.

Although the methods of the invention are advantageous in that complex biological samples can be analyzed directly, a sample can also be processed, if desired. For example, a blood sample can be fractionated to isolate particular cell types, for example, red blood cells, white blood cells, and the like. A serum sample can be fractionated to isolate particular types of proteins, for example, based on structural or functional properties such as serum proteins modified by glycosylation, phosphorylation, or other post-translational modifications, or proteins having a particular affinity, such as an affinity for nucleic acids. A serum sample can also be fractionated based on physical-chemical properties, for example, size, pI, and the like. A serum sample can additionally be fractionated to remove bulk proteins present in large quantities, such as albumin, to facilitate analysis of less abundant serum polypepties. Furthermore, a cellular sample can be fractionated to isolate subcellular organelles. Moreover, a cellular or tissue sample can be solubilized and fractionated by any of the well known fractionation methods, including chromatographic techniques such as ion exchange, hydrophobic and reverse phase, size exclusion, affinity, hydrophobic charge-induction chromatography, and the like (Ausubel et al., supra, 1999; Scopes, *Protein Purification: Principles and Practice,* third edition, Springer-Verlag, New York (1993); Burton and Harding, *J. Chromatogr. A* 814:71–81 (1998)).

Although the methods of the invention are particularly useful for analyzing complex samples such as biological samples, the methods can also be used on samples of reduced complexity. For example, the sample can be fractionated, as described above, to provide a smaller number of sample molecules to be captured on solid phase, including prior affinity chromatography. In addition, the sample can be a highly purified sample, including essentially a single purified molecule such as a polypeptide or nucleic acid or molecule that is expressed at high levels in the sample, for example, by recombinant methods.

The methods of the invention can be readily adapted to automation. For example, automated sampling, robotics, or any suitable automation methods can be applied to methods of the invention, if desired. Since all the reactions can be done easily in an automated fashion, the methods permit a high throughput sample preparation. In addition, since there is virtually no sample handling such as transferring steps, loss of captured molecules is minimized, thus improving the yield of molecule recovery. The captured molecules can also be extensively washed to remove non-captured sample molecules or any regents since the captured sample molecules remain bound to the solid support during the wash steps. The methods of the invention can be used to capture essentially all of a class or multiple classes of molecules from a sample, or a portion of the molecules from a sample, as desired.

The methods of the invention can be used to determine the expression level of molecules in a sample. The expression level refers to the amount of a molecule in a sample. The expression level of a molecule can be representative of the amount of messenger RNA (mRNA) encoded by a gene, the amount of polypeptide corresponding to a given amino acid sequence encoded by a gene, or the amount of a biochemical form of a molecule accumulated in a cell, including, for example, the amount of particular post-synthetic modifications of a molecule such as a polypeptide, nucleic acid or small molecule. The expression level can refer to an absolute amount of a molecule in a sample or to a relative amount of the molecule compared to a standard, including amounts determined under steady-state or non-steady-state conditions. The expression level of a molecule can be determined relative to a control component molecule in a sample. The expression level can be determined by direct comparison of two or more samples, as disclosed herein (see Example III).

As disclosed herein, the solid phase can be a glass bead such as a controlled pore glass bead (see Example I). However, any suitable solid support useful for binding sample molecules and carrying out the desired chemistry and washing conditions can be used. The solid support can thus be glass, derivatized glass, silicon, plastic or other substrates. Any solid phase materials suitable for solid phase chemical synthesis are useful as solid supports in methods of the invention. The solid supports can be porous or non-porous materials, surface films, magnetic beads, colloids, membranes and the like. The solid supports can be in the form of beads, flat surfaces, or any configuration suitable for capturing molecules using the methods disclosed herein. The solid support can be derivatized to incorporate chemical moieties suitable for coupling to other chemical groups, as desired.

It is understood that modifications which do not substantially affect the activity of the various embodiments of this invention are also included within the definition of the invention provided herein. Accordingly, the following examples are intended to illustrate but not limit the present invention.

EXAMPLE I

Attachment of Cysteine-containing Peptide to a Solid Support and Recovery

This example describes the attachment of a cysteine-containing peptide to beads and recovery of a modified peptide by photo-cleavage.

Figure 2A:
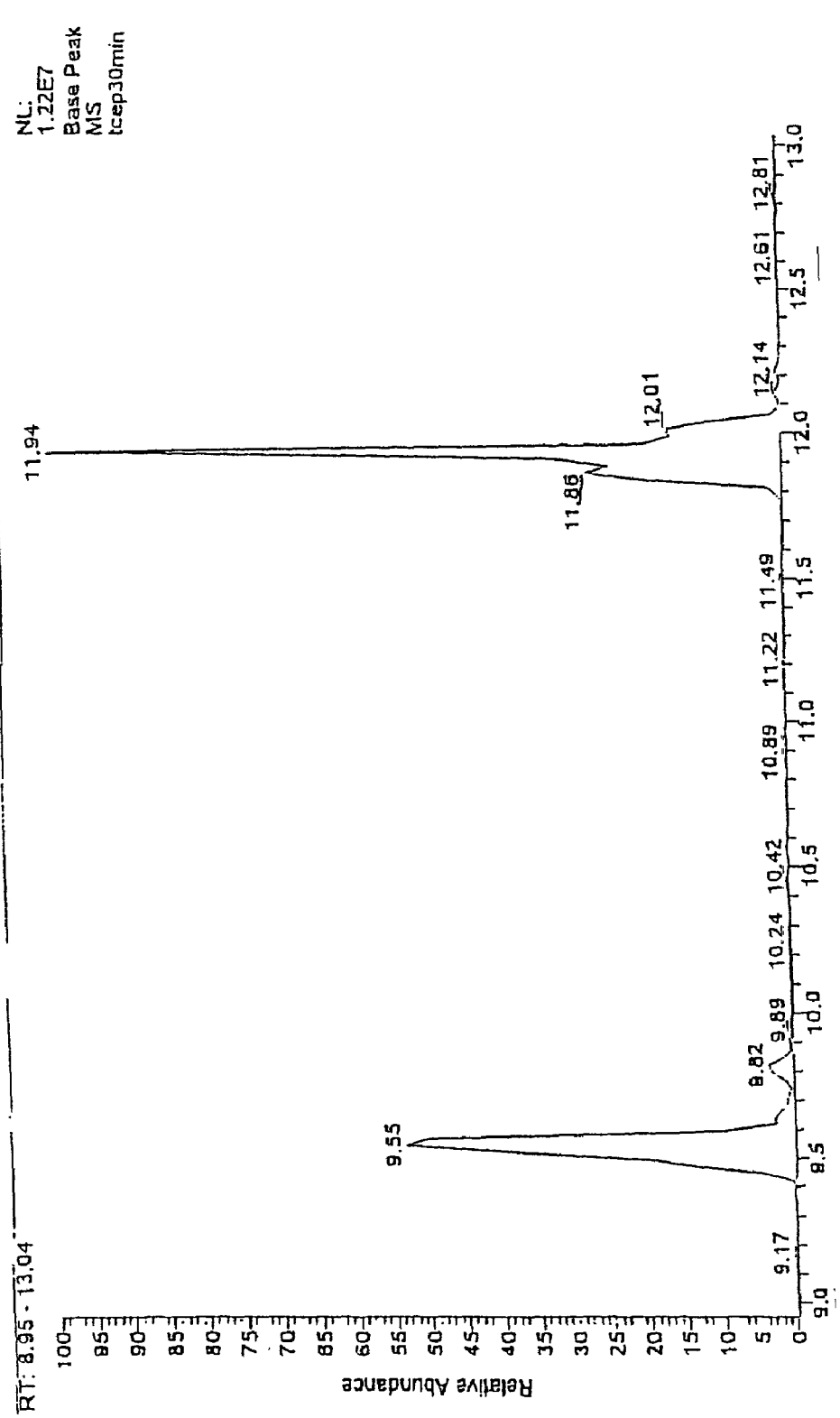
FIG. 2A shows LC analysis by reverse phase HPLC of a mixture of laminin B and control phosphoangiotensin.
Figure 2B:
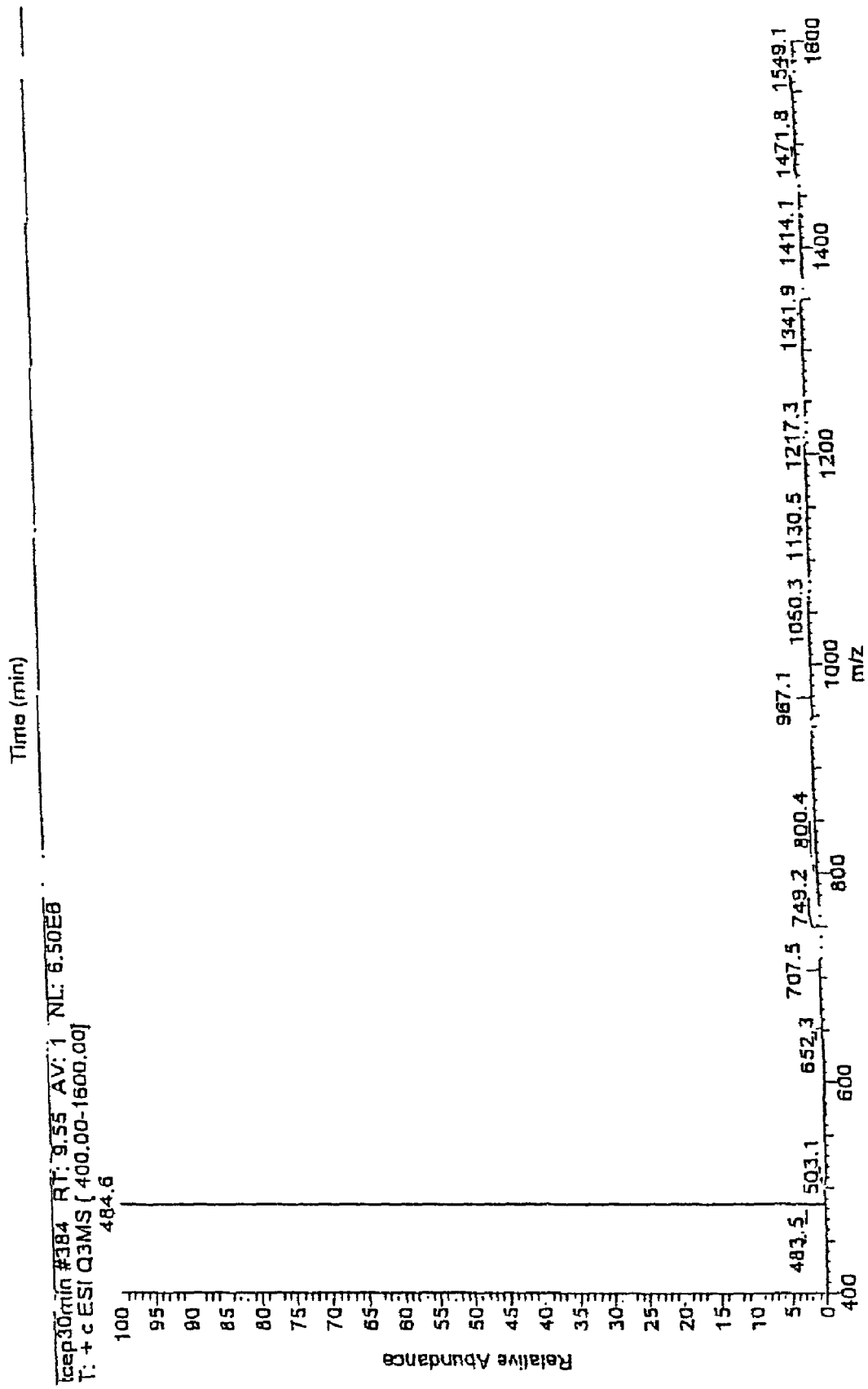
FIG. 2B shows electrospray ionization MS analysis of TCEP treated laminin B.

A schematic diagram illustrating the attachment of a cysteine-containing peptide to the solid phase beads and recovery of the modified peptide via photo-cleavage is shown in FIG. 1. To demonstrate the capture and modification of a cysteine-containing peptide, commercially available laminin B peptide with the sequence CDPGYIPSR (SEQ ID NO:1; molecular weight 967) was used. The peptide was analyzed by liquid chromatography on reverse phase HPLC and mass spectrometry (LC-MS). The peptide was reduced by tris(2-carboxyethyl)phosphine (TCEP) and detected as a single peak eluting at 9.55 min with a mass to charge ratio (m/z) of m/z=484.6 for a doubly charged ion, as expected (see FIG. 2). A second peak eluting at 11.94 min is another standard peptide, namely phosphoangiotensin, with the sequence DRVYIHPF (SEQ ID NO:2; molecular weight 1126) that was added to the sample as a control. Phosphoangiotensin does not contain cysteine and was observed with the expected mass.

A solid phase support bead of controlled pore glass was modified by covalently attaching a photo-cleavable linker with an amino functionality (see FIG. 1). The photocleavable linker was attached to the solid support via a silane linkage. The reactive group is an iodoacetyl group that specifically reacts with sulfhydryl groups. Briefly, glass beads functionalized with amino groups (Sigma Aldrich; St Louis Mo.) were used as the solid support. Fmoc protected photolinker (4-[4-(1-(Fmocamino)ethyl)-2-methoxy-5-nitrophenoxy) butanoic acid or Fmoc-aminoethyl-photolinker;

NovaBiochem, affiliate of Merck KGaA; Darmstadt Germany) and leucine were attached sequentially to the amino group functionalized beads via carbodiimide chemistry under standard solid phase peptide synthesis procedures. Fmoc protection on the leucine was then removed by piperidine treatment, and the free α-amino group of leucine was reacted with iodoacetic anhydride to create the reactive iodoacetyl group.

Figure 3A:
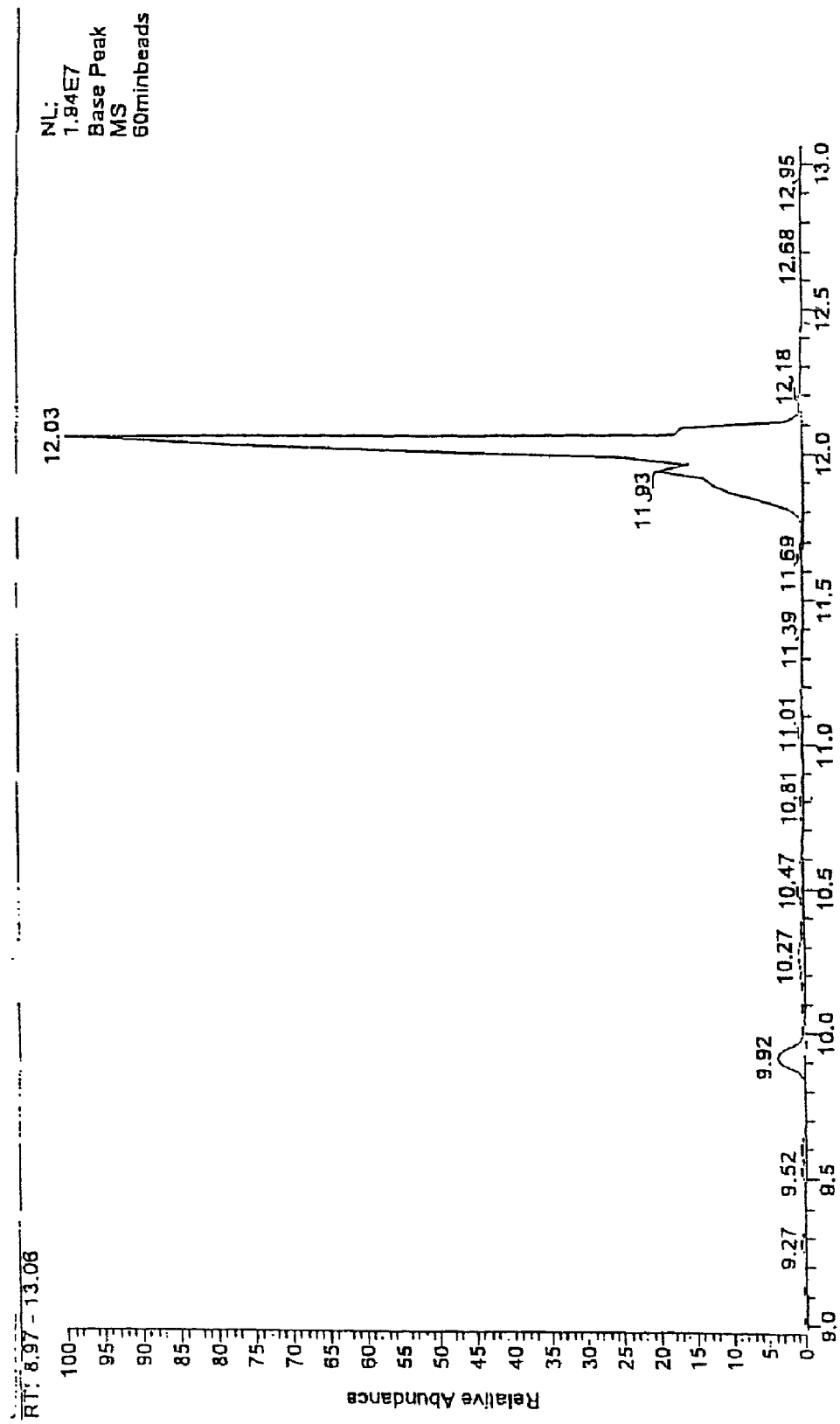
FIG. 3A shows LC analysis of an aliquot of the supernatant as treated in FIG. 2.
Figure 3B:
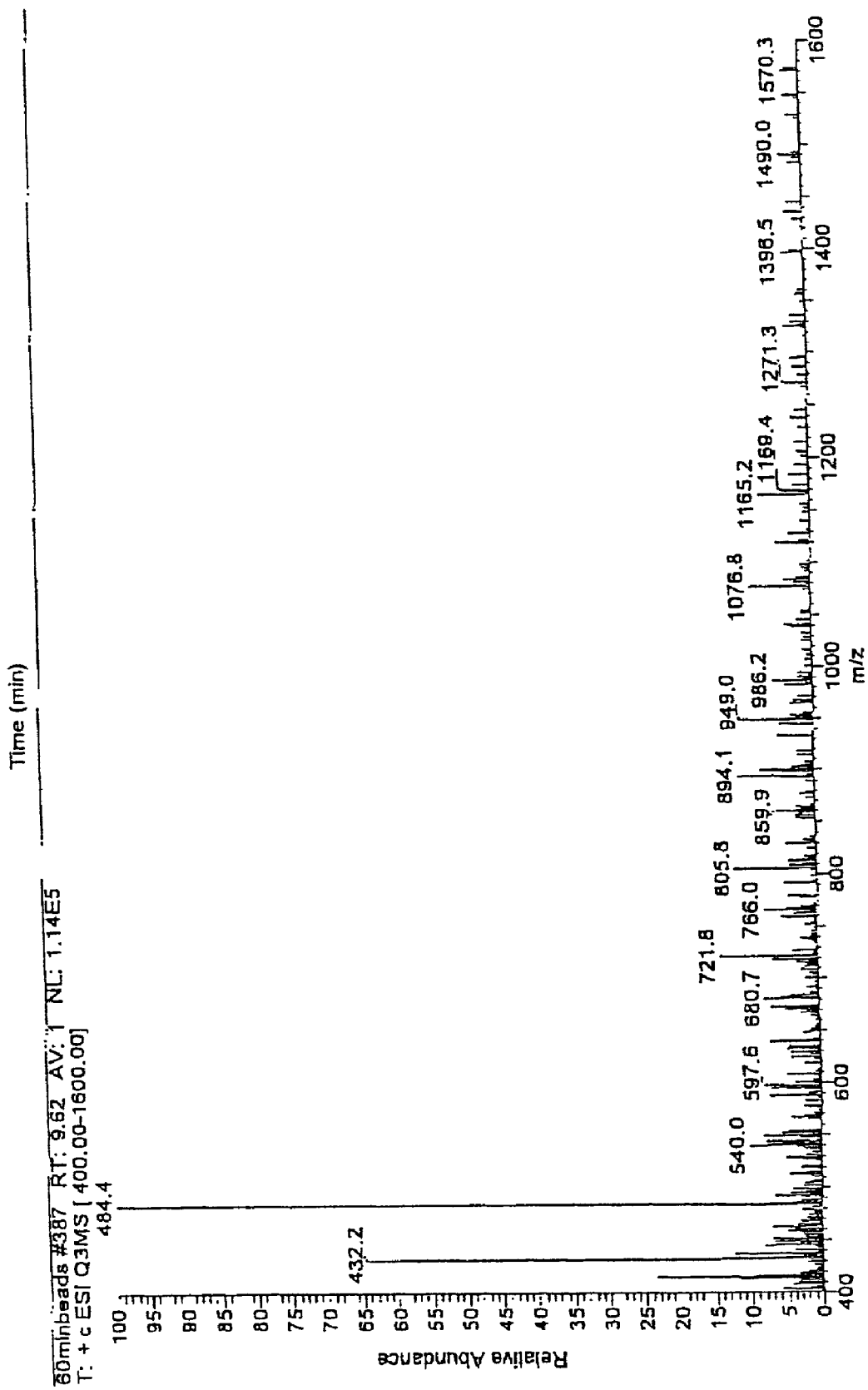
FIG. 3B shows MS analysis of the 9.62 min LC fraction of FIG. 3A having a retention time consistent with reduced laminin B. The amount of laminin B was reduced due to binding to beads.

After incubating the peptides with the beads, as shown in FIG. 1, an aliquot of the supernatant was again analyzed by LC-MS. Data are shown in FIG. 3. As expected, only the non-cysteine containing phosphoangiotensin peptide was present in the supernatant, while the cysteine-containing laminin B peptide had disappeared completely from the solution, presumably due to quantitative capture by the beads.

Figure 4A:
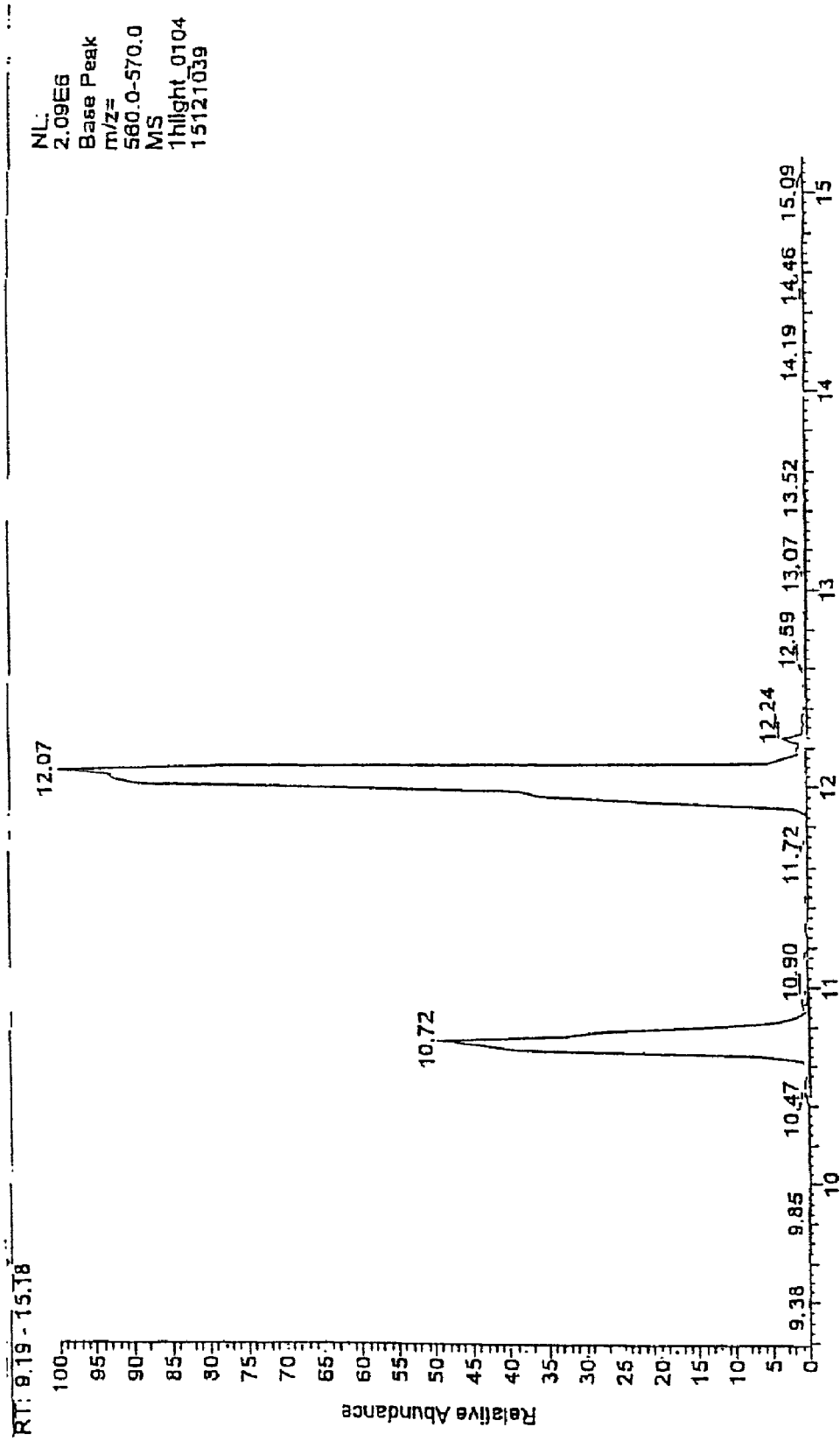
FIG. 4A shows LC analysis of photo-cleaved laminin B, with the addition of control phosphangiotensin at a concentration equivalent to the amount used in FIG. 2.
Figure 4B:
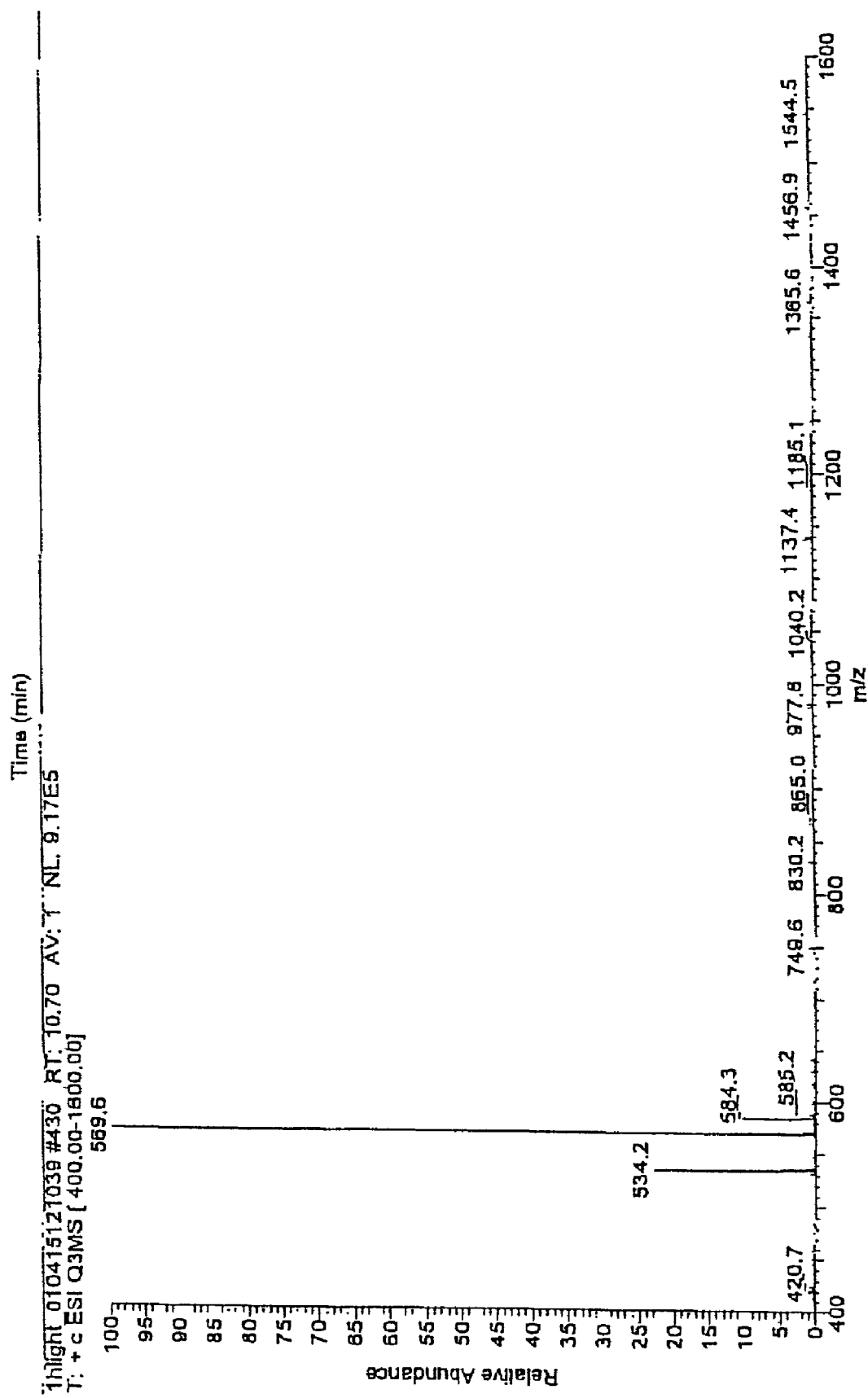
FIG. 4B shows MS analysis of the photo-cleaved laminin B peak eluting at 10.72 min in FIG. 4A, with the expected increase in mass due to modification.

After washing the beads with 2M sodium chloride, methanol, and water, the beads were resuspended in buffer containing 0.2M Tris, pH 8.0, 10 mM ethylenediaminetetraacetic acid (EDTA), again with the same concentration of phosphoangiotensin peptide spiked in as a control. The beads were exposed to 360 nm ultraviolet light for photocleavage. After photo-cleavage, the laminin B peptide with the expected mass modification (m/z=569 for [M+2H]2+ ion) was observed at a slightly slower elution time (10.72 min) compared to the initial laminin B peptide (FIG. 4). The longer retention time is consistent with the reduced polarity of the expected photo-cleaved product due to the addition of the transferred leucine amino acid. The structure of the photo-cleaved product was further confirmed by MS/MS sequencing analysis. The relative peak intensities of the modified laminin B peptide and phosphoangiotensin standard gave a rough estimate of the photo cleavage efficiency. At least 50 percent of the laminin B peptide originally input was recovered. The yield can be improved by further optimization of the capture and release reactions.

These results demonstrate the successful transfer of the amino acid leucine to the sulfhydryl side chain of a peptide via capture-and release chemistry. These results exemplify a general approach to selectively capture peptides and transfer functional groups such as amino acids to the peptides.

EXAMPLE II

Modification of an Amino Group of a Polypeptide to Incorporate a Sulfydryl Group This example describes the N-terminal modification of a peptide to incorporate a sulfhydryl group.

Figure 5:
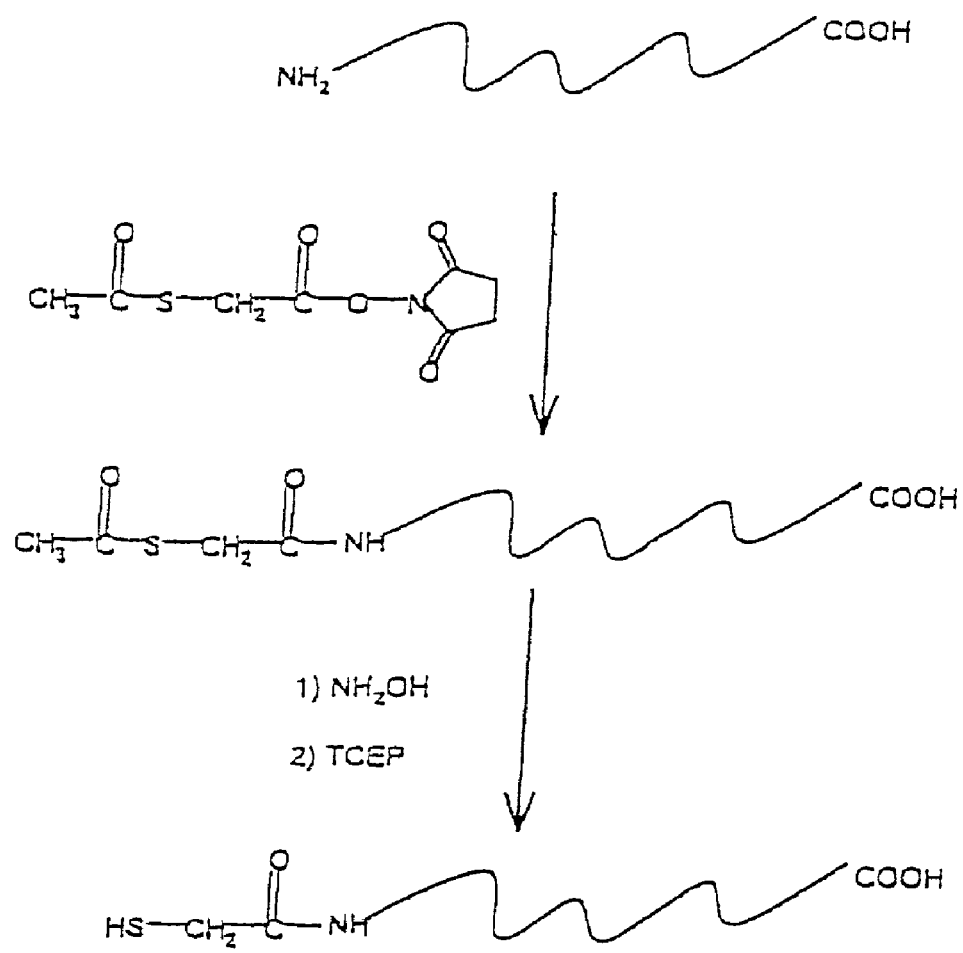
FIG. 5 shows a strategy for tagging of the primary amine groups of a polypeptide to incorporate a sulfhydryl group. The amino group(s) of a polypeptide is/are modified by N-succinimidyl S-acetylthioacctate (SATA). Upon hydroxylamine treatment, followed by reduction with tris(2-carboxyethyl)phosphine (TCEP), the amino group of the polypeptide is converted into a sulfhydryl group.

In cases in which peptides do not contain cysteine residues, the peptide can be modified to incorporate a sulfhydryl group, allowing conversion of an amino group to a sulfhydryl group and capture of the peptide via the incorporated sulfhydryl group. The strategy for modification of an amino group of a polypeptide is illustrated in FIG. 5.

Phosphoangiotensin was used to demonstrate the principle of modifying an amino group to a sulfhydryl group. The peptide was first modified by N-succinimidyl S-acetylthioacetate (SATA), which is reactive towards primary amine specifically. Phosphoangiotensin was modified as shown in FIG. 5. Briefly, phosphoangiotensin was incubated with 10 mM SATA for 30 min in 0.1 M $K_3PO_4$, pH 8.0, at room temperature.

Figure 6A:
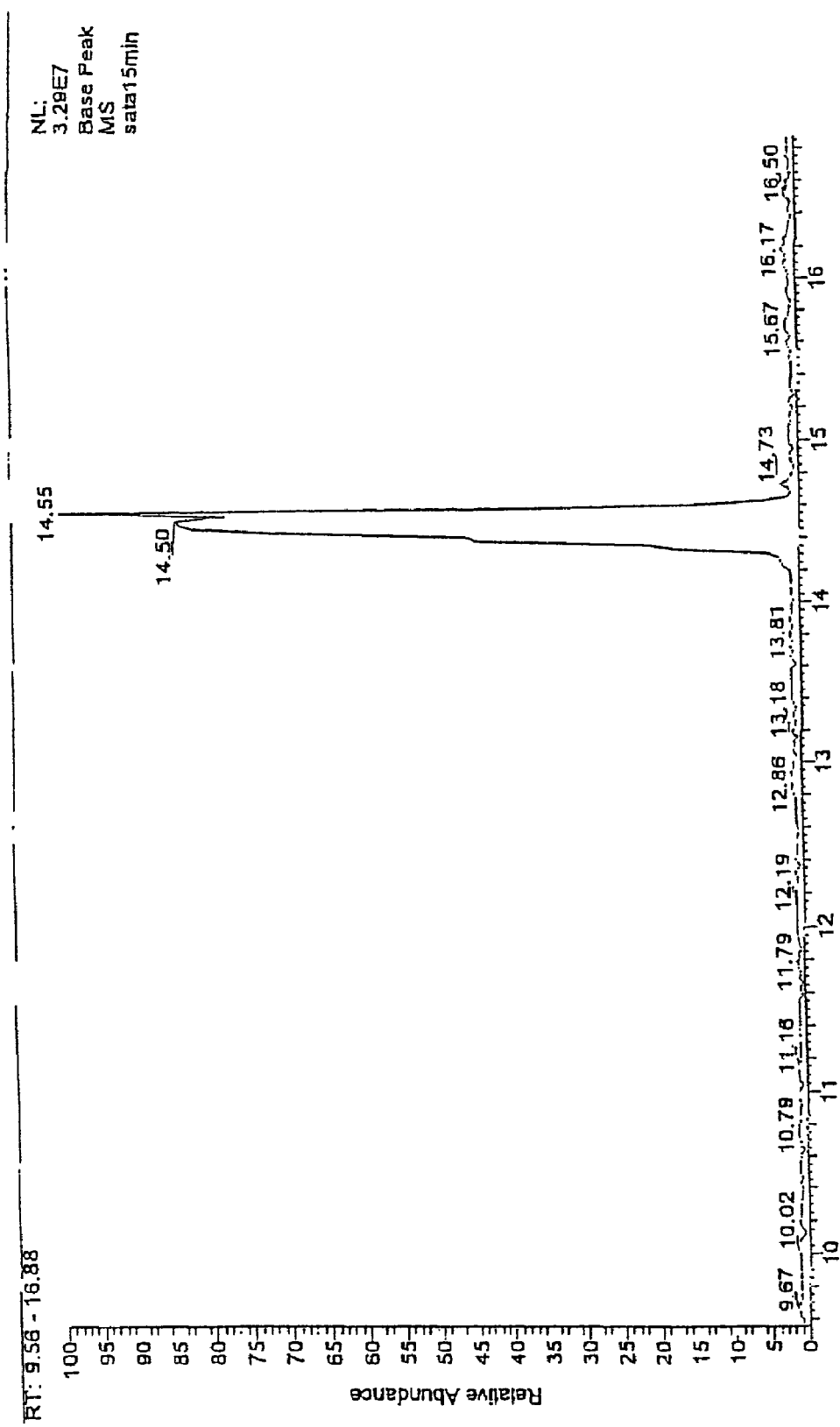
FIG. 6A shows LC analysis of SATA treated phosphoangiotensin.
Figure 6B:
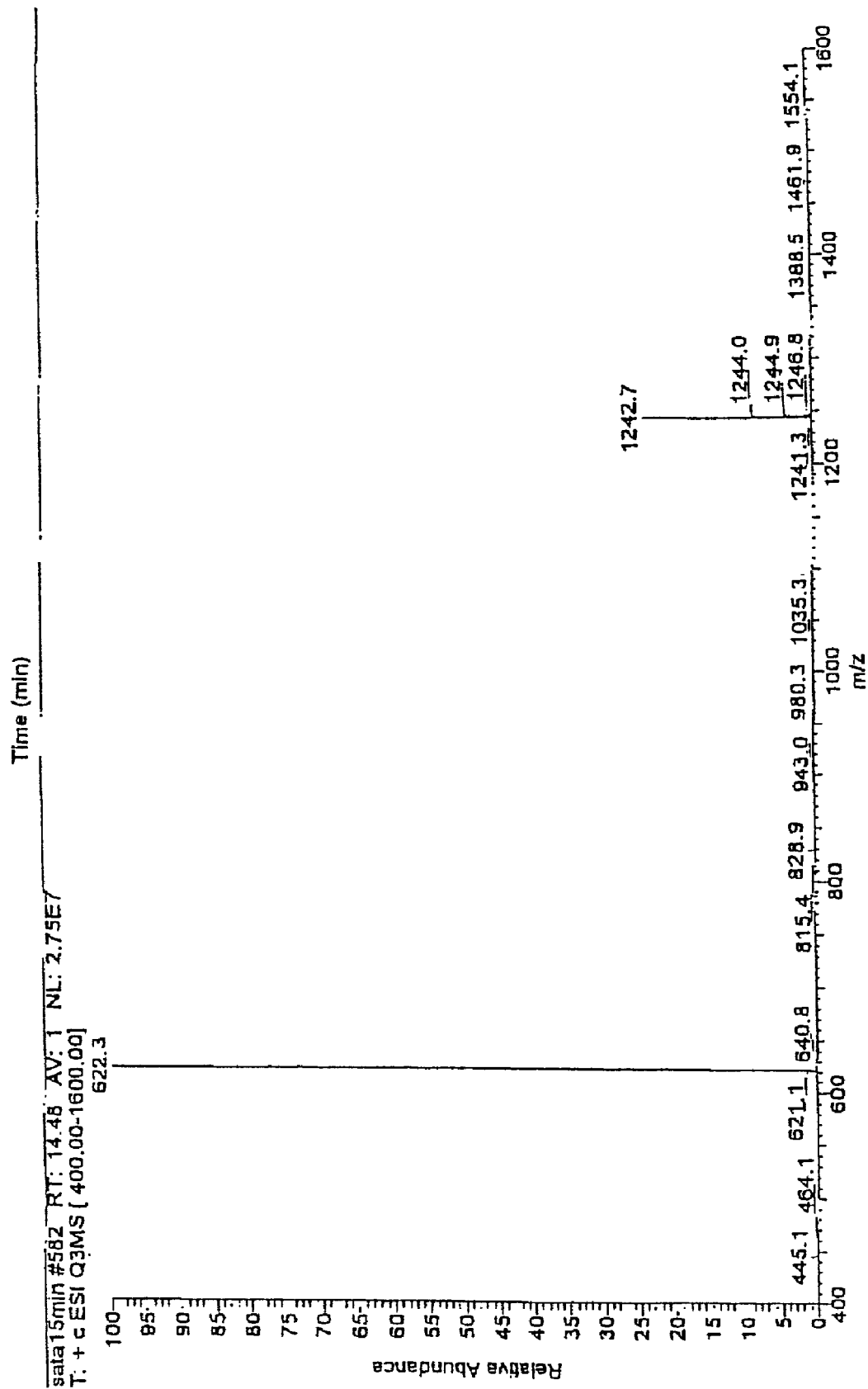
FIG. 6B shows MS analysis of the SATA treated phosphoangiotensin. The two main signals represent the singly charged, [M+H]+=1242.7 mass units, and doubly charged, [M+2H]2+=622.3 mass units, forms.

The modified phosphoangiotensin was analyzed by LC-MS. The N-terminal modification of the peptide was observed. The data shown in FIG. 6 indicate that a single product eluted at 14.5–14.55 min with m/z=622.3 for [M+2H]2+ions. The measured mass correlated well with the calculated mass for SATA derivatized phosphoangiotensin peptide (m/z=622.3).

Figure 7A:
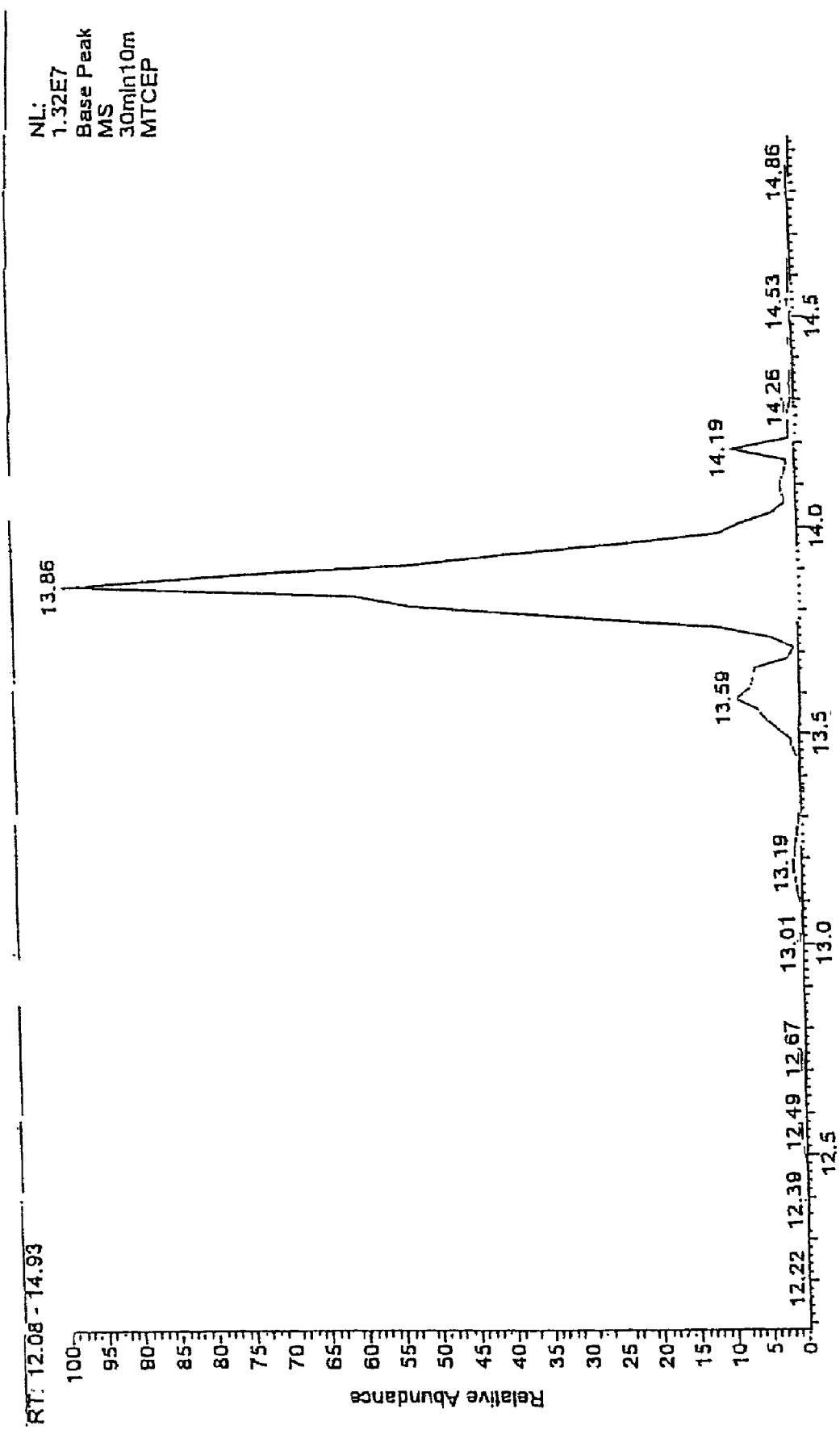
FIG. 7A shows LC analysis of the reduced modified phosphoangiotensin.
Figure 7B:
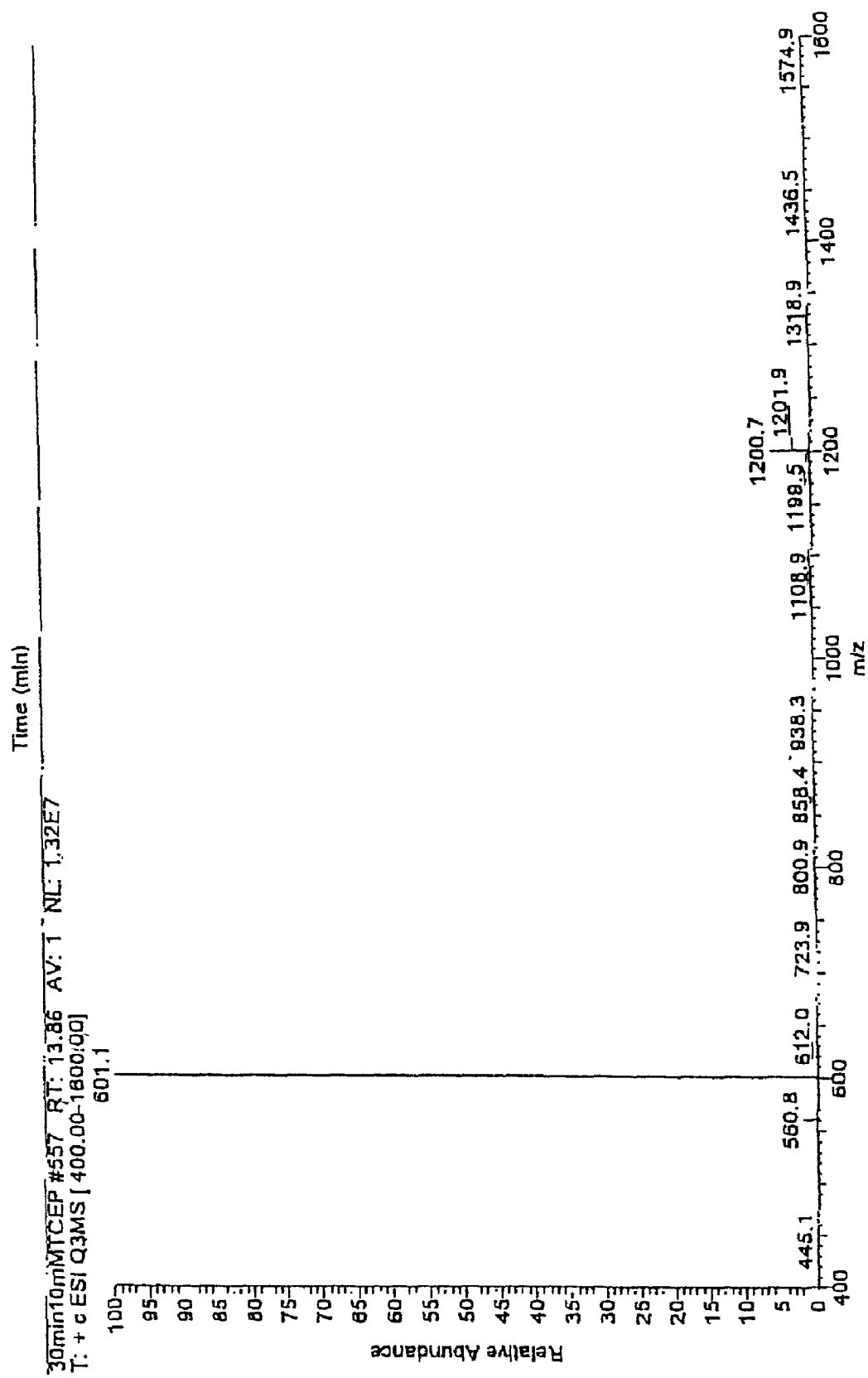
FIG. 7B shows MS analysis of the reduced modified phosphoangiotensin, indicating the expected change in mass due to the modification. The two main signals represent the singly charged, [M+H]+=1200.7 mass units, and doubly charged, [M+2H]2+=601.1 mass units, forms.

The modified peptide was treated with 0.1 M hydroxylamine at pH 8 for 2 hours, followed by reduction with 5 mM TCEP for 30 min. As indicated in FIG. 5, treatment by hydroxylamine and reduction by TCEP generate a free SH group in the SATA-derivatized phosphoangiotensin. Data from the LC-MS analysis of such a treated compound is shown in FIG. 7. Again, a single product eluting at 13.86 min was observed. MS analysis indicated m/z=601 for [M+2H]2+ions. The measured mass agreed with the calculated mass for the expected peptide product (m/z=601). Thus, conversion of amino groups of peptides into free SH groups can be made quantitatively with a minimal amount of side products. Furthermore, such a sulfhydryl modified polypeptide can be subsequently captured as described in Example I.

These results demonstrate that an amino group of a polypeptide can be essentially quantitatively modified to incorporate a sulfhydryl group.

EXAMPLE III

Analysis of Protein Samples by Incorporation of Heavy and Light Labels

This example describes differential labeling of two samples for qualitative and quantitative analysis of sample polypeptides by mass spectrometry.

Figure 8:
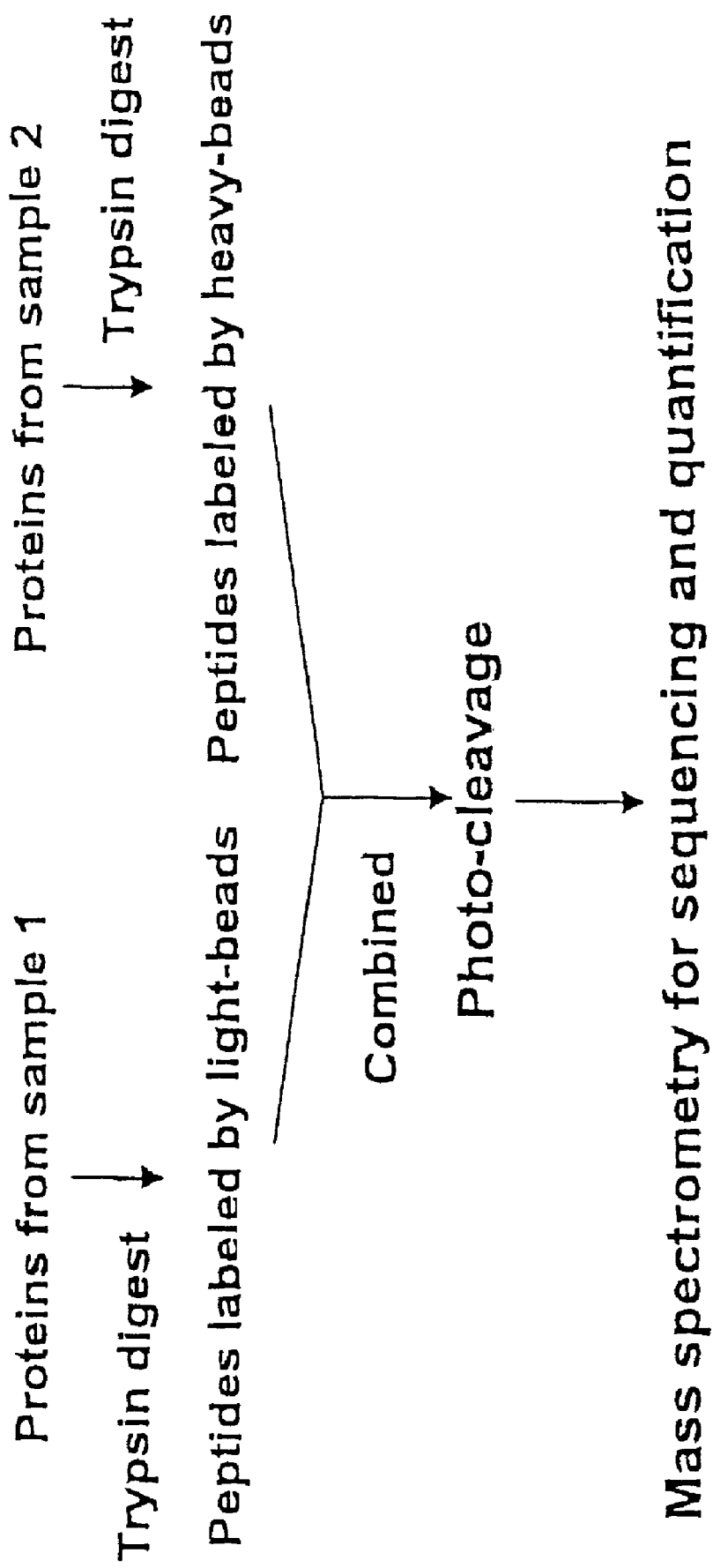
FIG. 8 shows a schematic outline for comparison of two samples by differential modification using solid phase capture.

A schematic diagram of the differential labeling of polypeptides is shown in FIG. 8. The samples are digested with a protease such as trypsin. The digested polypeptides are treated as described in Example I. If desired, the sample polypeptides can be modified by the method described in Example II to examine polypeptides lacking cysteine.

One digested sample is added to beads covalently attached to a chemical group containing a non-deuterated amino acid such as leucine or another suitable amino acid. The second sample is added to beads covalently attached to a chemically identical group except that the chemical group contains a deuterated form of the same amino acid. The differentially isotopically labeled leucine differs in mass by 7 or 10 mass units, depending on the state of deuteration of leucine.

After covalently coupling the sample polypeptides to the respective beads containing differentially isotopically labeled amino acids, the beads are combined and then cleaved by photo-cleavage. The photo-cleaved polypeptides, now differentially labeled, are analyzed simultaneously by mass spectrometry. MS can be used for quantitation of the samples by direct comparison of the intensities of MS signals from the two samples, which differ by a predetermined mass and can be readily distinguished on MS as doublet peaks differing by the predetermined mass. In addition, the samples can be sequenced by MS.

This example demonstrates differential labeling and analysis of sample molecules by mass spectrometry.

EXAMPLE IV

Modification of Captured Phosphopeptides

This example describes the capture of polypeptides and modification of captured phosphopeptides.

Polypeptides from a sample are captured on beads essentially as described in Example I. The captured polypeptides are modified essentially as described in Zhou et al., *Nature Biotechnol.* 19:375–378 (2001), which is incorporated herein by reference.

Briefly, the captured polypeptides are modified by the following steps. (1) Amino protection: peptide amino groups are optionally protected using t-butyl-dicarbonate (tBoc) chemistry to eliminate the potential for intra- and intermolecular condensation in subsequent reactions. (2) Condensation reaction: carbodiimide catalyzes condensation reactions between the peptides and excess amine to form amide and phosphoramidate bonds at the carboxylate and phosphate bonds of the peptides, respectively. (3) Phosphate regeneration: free phosphate groups are regenerated by brief acid hydrolysis of the phosphoramidate bonds. (4) Condensation and reduction: a carbodiimide-catalyzed condensation reaction attaches a cystamine to the regenerated phosphate group(s). Reduction of the internal disulfide of cystamine next generates a free sulfhydryl group for every phosphate of the captured phosphopeptides. (5) Release of modified polypeptides: the captured polypeptides are released from the solid support by cleavage of the chemical cleavage group, for example, using light as described in Example I. (6) Solid-phase capture: the released polypeptides, including the modified phosphopeptides containing a free sulfhydryl, are attached to a second solid phase by reacting the free sulfhydryl groups in the peptides with iodoacetyl groups immobilized on glass beads. (7) Phosphopeptide recovery: following stringent washing of the resin, phosphopeptides are recovered by cleavage of phosphoramidate bonds using trifluoracetic acid (TFA) at a concentration that also removes the tBoc protection group, thus regenerating peptides with free amino and phosphate groups. The carboxylate groups remain blocked from step (2).

The chemical reactions are carried out as described below in more detail. The solid phase containing captured polypeptides is incubated in 50% (vol/vol) of 0.1 M phosphate buffer, pH 11, and acetonitrile. 0.1 M tBoc is added for 4 h at room temperature. Acetonitrile is then removed. The solid phase containing captured polypeptides is incubated in 1M ethanolamine, 25 mM N-hydroxysuccinimide (NHS), and 0.5 M of N,N'-dimethylaminopropyl ethyl carbodiimide HCL (EDC) and incubated for 2 h at room temperature. 10% TFA is added and incubated 30 min at room temperature. The solid phase is washed to remove excess reagents and to desalt, and 1 M imidazole, pH 6.0, is added. 0.5 M EDC is added for 3 hours at room temperature. The solid phase is washed and then incubated with 1 M cystamine, pH 8.0, for 2 h at 50° C. The solid phase is washed with water and then reduced with 10 mM dithiothreitol (DTT) to generate free sulfhydryl groups. The solid phase is washed to remove DTT, and then the captured molecules are released by cleavage of the cleavable functional group.

The released polypeptides, including the phosphopeptides modified with sulfhydryl groups, are incubated for at least 2 h with a second type of solid phase beads, which have iodoacetyl groups and are titrated to pH 8.0 with 1 M Tris, pH 8.0, 50 mM ethylenediamine tetraacetic acid (EDTA). Beads with immobilizede iodoacetyl groups are prepared by a 2 h reaction between 3 equivalents of iodoacetic anhydride and 1 equivalent of amino beads (G4643; Sigma; St. Louis Mo.) with 3.3 equivalents of diisopropylethylamine in dimethylformide. Since a tyrosine adduct with carbodiimide is a possible side reaction, the captured phosphopeptides modified with sulfhydryl groups are incubated in 1 M hydroxylamine, pH 10, for 2 h at room temperature to restore any modified tyrosines. The beads are then washed sequentially with 2 M NaCl, methanol and water to remove nonspecifically bound molecules. The beads are incubated with 100% TFA for 30 min to recover phosphopeptides and concurrently remove tBoc protection from tBoc modified groups. The recovered phosphopeptides are then analyzed, for example, by mass spectrometry.

The molecules captured on the first solid support are generally released just prior to re-capture on the second solid phase, which selectively captures the modified phosphopeptides, allowing efficient washing and removal of chemicals used to modify the captured polypeptides. However, the peptides can be released at an earlier stage, even after the initial capture, if binding to the first solid phase is intended only to transfer a label or tag to the captured polypeptides. Alternatively, the modification of phosphopeptides can be carried out essentially as described in Zhou et al., and then the recovered phosphopeptides captured and labeled essentially as described in Example I.

This example demonstrates the selective modification and isolation of phosphopeptides.

Throughout this application various publications have been referenced. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention.

What is claimed is:

1. A composition comprising a solid support coupled to a chemical group comprising a cleavable functional group, a tag and a reactive group covalently linked to a sample molecule, wherein said cleavable functional group is covalently coupled to said solid support, said tag is covalently coupled to said cleavable functional group, and said reactive group is covalently coupled to said tag and wherein said cleavable functional group, said tag and said reactive group are positioned relative to each other to allow transfer of said tag to said sample molecule and release of said sample molecule from said solid support upon cleavage of said cleavable functional group.

2. The composition of claim 1, wherein said sample molecule is selected from the group consisting of a polypeptide, a nucleic acid, a lipid, a second messenger, and a metabolite.

3. The composition of claim 2, wherein said sample molecule is a polypeptide.

4. The composition of claim 3, wherein said polypeptide has a modification selected from the group consisting of phosphorylation, glycosylation, ubiquitination, acetylation, palmitylation, prenylation, sulfation, hydroxylation, and myristylation.

5. The composition of claim 4, wherein said polypeptide is a phosphopolypeptide.

6. The composition of claim 1, wherein the solid support is a glass bead.

7. The composition of claim 1, wherein said cleavable functional group is a chemical linker cleavable by light, an acid, a base or an enzyme.

8. The composition of claim 1, wherein said tag is a mass spectrometry tag.

9. The composition of claim 1, wherein said tag is selected from the group consisting of a stable isotope tag, an isotope distribution tag, and a charged amino acid.

10. The composition of claim 9, wherein said tag is a stable isotope coded amino acid.

11. The composition of claim 10, wherein said tag is a deuterated or non-deuterated amino acid.

12. The composition of claim 1, wherein said tag comprises an element having a characteristic isotope distribution.

13. The composition of claim 1, wherein said covalently linked reactive group is derived from a succinimide ester group or an iodoacetyl group.

14. The composition of claim 3, wherein a primary amine group of said polypeptide is modified by treatment with N-succinimidyl S-acetylthioacctate, hydroxylamine, and tris (2-carboxyethyl) phosphine.

15. A composition comprising a solid support covalently coupled to a chemical group comprising a cleavable functional group, a mass spectrometry tag and a reactive group for covalently attaching a sample molecule, wherein said cleavable functional group is covalently coupled to said solid support, said tag is covalently coupled to said cleavable functional group, and said reactive group is covalently coupled to said tag and wherein said cleavable functional group, said tag and said reactive group are positioned relative to each other to allow transfer of said tag to a sample molecule attached to said reactive group upon cleavage of said cleavable functional group and release of said sample molecule from said solid support.

16. The composition of claim 15, wherein the solid support is a glass bead.

17. The composition of claim 15, wherein said cleavable functional group is a chemical linker cleavable by light, an acid, a base or an enzyme.

18. The composition of claim 15, wherein said tag is selected from the group consisting of a stable isotope tag, an isotope distribution tag, and a charged amino acid.

19. The composition of claim 18, wherein said tag is a stable isotope coded amino acid.

20. The composition of claim 19, wherein said tag is a deuterated or non-deuterated amino acid.

21. The composition of claim 15, wherein said tag comprises an element having a characteristic isotope distribution.

22. The composition of claim 15, wherein said reactive group of said chemical group is selected from the group consisting of a succinimide ester group and an iodoacetyl group.

23. The composition of claim 15, wherein said cleavable group is a photocleavable group, said functional group is a mass tag, and said reactive group reacts with a sulfhydryl group.

24. The composition of claim 23, wherein said sample molecule is selected from the group consisting of a polypeptide, a nucleic acid, a lipid, a second messenger, and a metabolite.

25. The composition of claim 24, wherein said sample molecule is a polypeptide.

26. The composition of claim 25, wherein said polypeptide has a modification selected from the group consisting of phosphorylation, glycosylation, ubiquitination, acetylation, palmitylation, prenylation, sulfation, hydroxylation, and myristylation.

27. The composition of claim 26, wherein said polypeptide is a phosphopolypeptide.

28. The composition of claim 23, wherein the solid support is a glass bead.

29. The composition of claim 23, wherein said mass tag is an amino acid.

30. The composition of claim 29, wherein said mass tag is leucine.

31. The composition of claim 23, wherein said mass tag is selected from the group consisting of a stable isotope tag, an isotope distribution tag, and a charged amino acid.

32. The composition of claim 31, wherein said mass tag is a stable isotope coded amino acid.

33. The composition of claim 32, wherein said mass tag is a deuterated or non-deuterated amino acid.

34. The composition of claim 23, wherein said mass tag comprises an element having a characteristic isotope distribution.

35. The composition of claim 23, wherein said reactive group is an iodoacetyl group.

36. The composition of claim 23, wherein said photocleavable group comprises amino(ethyl)-2-methoxy-5-nitrophenoxy.

37. The composition of claim 25, wherein a primary amine group of said polypeptide is modified by treatment with N-succinimidyl S-acetylthioacctate, hydroxylamine, and tris (2-carboxyethyl) phosphine.

38. A composition having the structure

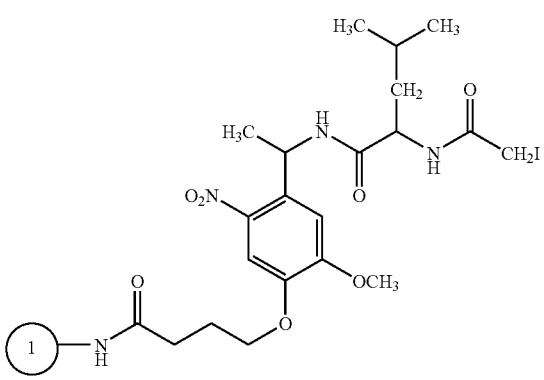

wherein (1) represents a solid support, wherein the leucyl group of said structure contains an isotope tag and wherein the I reactive group is covalently linked to a sulfhydryl group of a sample molecule.

39. The composition of claim 38, wherein said sample molecule is selected from the group consisting of a polypeptide, a nucleic acid, a lipid, a second messenger, and a metabolite.

40. The composition of claim 39, wherein said sample molecule is a polypeptide.

41. The composition of claim 40, wherein said polypeptide has a modification selected from the group consisting of phosphorylation, glycosylation, ubiquitination, acetylation, palmitylation, prenylation, sulfation, hydroxylation, and myristylation.

42. The composition of claim 41, wherein said polypeptide is a phosphopolypeptide.

43. The composition of claim 38, wherein the solid support is a glass bead.

44. The composition of claim 40, wherein a primary amine group of said polypeptide is modified by treatment with N-succinimidyl S-acetylthioacctate, hydroxylamine, and tris(2-carboxyethyl)phosphine.

45. The composition of claim 15, wherein said isotope tag is selected from the group consisting of a stable isotope tag and an isotope distribution tag.

46. The composition of claim 45, wherein said isotope tag is deuterated or non-deuterated.

47. The composition of claim 15, wherein said isotope tag comprises an element having a characteristic isotope distribution.

48. A composition having the structure

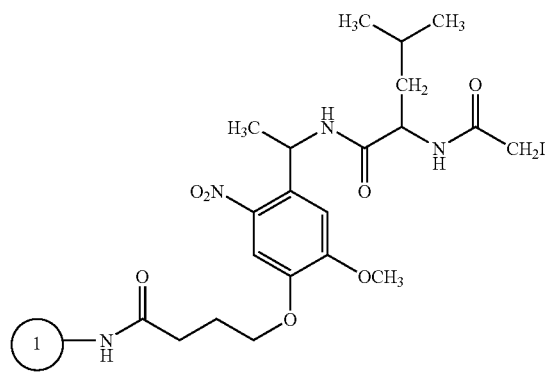

wherein (1) represents a solid support wherein the leucyl group of said structure contains an isotope tag and wherein I is a reactive group.

49. The composition of claim 48, wherein the solid support is a glass bead.

50. The composition of claim 48, wherein the leucyl group contains deuterium.

51. A composition containing a first and second composition, each of said first and second compositions having the structure

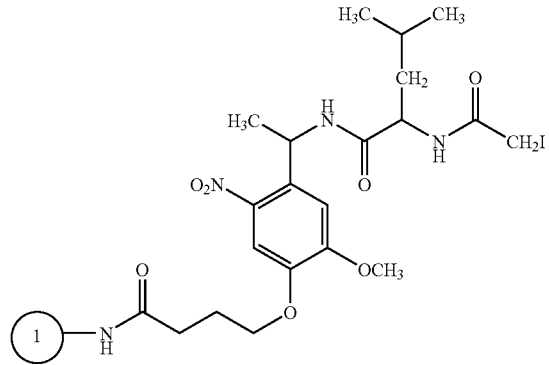

wherein (1) represents a solid support, wherein said first and second compositions are differentially isotopically labeled on the leucyl group and wherein I is a reactive group.

52. The compositions of claim 51, wherein said first composition is differentially isotopically labeled with deuterium.

53. The compositions of claim 51, wherein said first composition is differentially isotopically labeled with $^{13}C$.

54. The composition of claim 38, wherein the leucyl group contains $^{13}C$.

55. The composition of claim 48, wherein the leucyl group contains $^{13}C$.

56. The composition of claim 38, wherein the leucyl group contains deuterium.

57. The composition of claim 48, wherein the leucyl group contains deuterium.

* * * * *